US011851507B1

(12) United States Patent
Al Tarawneh et al.

(10) Patent No.: US 11,851,507 B1
(45) Date of Patent: Dec. 26, 2023

(54) METHOD OF MANUFACTURING STYRENE

(71) Applicant: United Arab Emirates University, Al Ain (AE)

(72) Inventors: Mohammednoor Al Tarawneh, Al Ain (AE); Toyin Shittu, Al Ain (AE); Abbas Khaleel, Al Ain (AE)

(73) Assignee: United Arab Emirates University, Al Ain (AE)

( * ) Notice: Subject to any disclaimer, the term of this patent is extended or adjusted under 35 U.S.C. 154(b) by 0 days.

(21) Appl. No.: 18/124,955

(22) Filed: Mar. 22, 2023

(51) Int. Cl.
*C08F 12/08* (2006.01)
*C08F 4/54* (2006.01)

(52) U.S. Cl.
CPC .............. *C08F 12/08* (2013.01); *C08F 4/545* (2013.01)

(58) Field of Classification Search
CPC ................................ C08F 12/08; C08F 4/545
See application file for complete search history.

(56) References Cited

U.S. PATENT DOCUMENTS

| 4,460,706 A | 7/1984 | Imanari et al. | |
| 4,647,427 A | 3/1987 | Liu | |
| 6,037,301 A * | 3/2000 | Min | C07B 31/00 502/202 |

FOREIGN PATENT DOCUMENTS

| CN | 1810367 | | 8/2006 | |
| CN | 108927156 A | * | 12/2018 | |
| CN | 110860284 A | * | 3/2020 | ......... B01J 23/42 |

OTHER PUBLICATIONS

Andressa Esteves da Silva, Rita Colemon Simoes, Raimundo Crisostomo Rabelo Neto, Lisiane V. Mattos, Renata O. da Fonseca, Matheus R. M. Signorelli, Fabio B. Noronha, Nickel / Doped Ceria Solid Oxide Fuel Cell Anodes for Dry Reforming of Methane, Journal of the Brazilian Chemical Society (Oct. 2014).

A.V. Shlyakhtina, L.G. Scherbakova, E.A. Nesterova, Accomodation of Niobium and Cerium Variable Valence Cations in the Crystal Lattice of the Ln23+Ti24+O7 (Ln=Dy, Yb) Pyrochlores, Inorganic Materials (Oct. 2013).

Gaylord D. Smith, Nathan C. Eisinger, The Effect of Niobium on the Corrosion Resistance of Nickel-Base Alloys, Niobium for High Temperature Applications, The Minerals, Metals, and Materials Society (2004).

Y. Kobayashi, Y. Fujiwara, Chemical Deposition of Cerium Oxide Thin Films on Nickel Substrate from Aqueous Solution, Journal of Alloys and Compounds, Feb. 2006, pp. 1157-1160, 408.

Maria Ziolek, Izabela Sobczak, The Role of Niobium Component in Heterogeneous Catalysts, May 1, 2017, pp. 211-225, vol. 285.

* cited by examiner

*Primary Examiner* — Thuan D Dang

(74) *Attorney, Agent, or Firm* — Boyle Fredrickson, S.C.

(57) ABSTRACT

A process of manufacturing styrene at atmospheric pressure with high selectivity (in the range of 91% to 96%) to styrene comprising: providing gaseous phenylacetylene; providing gaseous hydrogen; providing a cerium bimetallic catalyst comprising one of Ni-5% NbCe and Ni-10% NbCe; reducing the cerium bimetallic catalyst with hydrogen at 500° C. for about 2 hours; reacting the phenylacetylene with the hydrogen in the presence of the cerium bimetallic catalyst at a temperature of 300° C.; and thereby obtaining an end product comprising a styrene fraction of about 54% to 71% of the end product and a waste fraction. The catalyst is found to be stable for about 5 cycles of manufacturing styrene without losing selectivity to styrene and without reduced conversion rate.

11 Claims, 15 Drawing Sheets

(13 of 15 Drawing Sheet(s) Filed in Color)

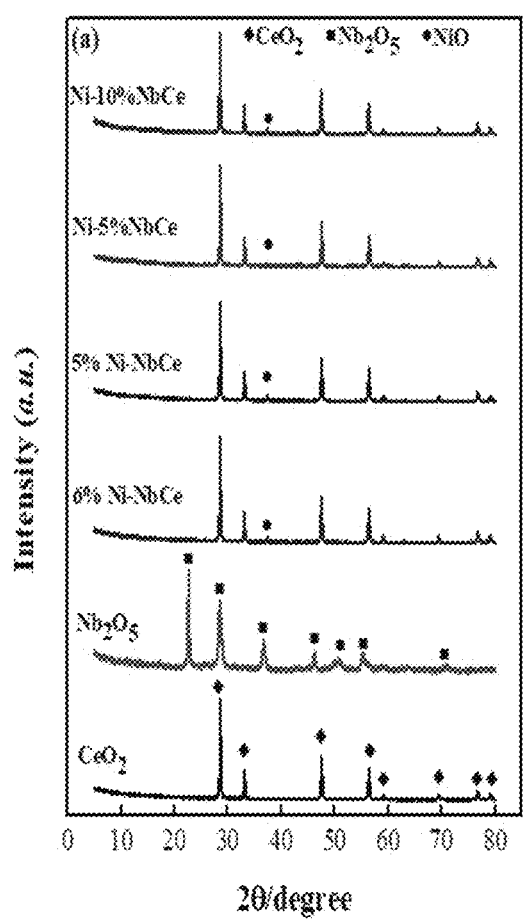 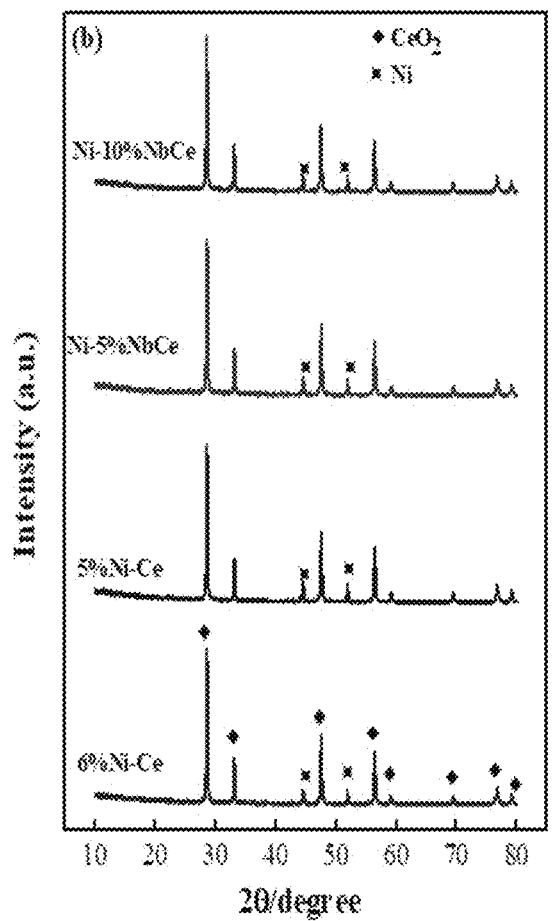
FIG.3 (a)  FIG.3 (b)

METHOD OF MANUFACTURING STYRENE

FIELD OF THE INVENTION

The invention is related to the field of manufacturing styrene. More specifically, the invention relates to a method of low temperature manufacturing of styrene using phenylacetylene as a raw material.

BACKGROUND OF THE INVENTION

Styrene based products are in continuous demand because of their importance as a monomer for the production of synthetic foam, plastics, rubbers, and polystyrene such as acrylonitrile butadiene styrene (ABS) and styrene butadiene (SB) latex. The market for styrene continues to expand with the current yearly output estimated at 30 million tons. Traditional production of styrene involves dehydrogenation of ethylbenzene over iron oxide catalysts, and/or the epoxidation of propylene with ethylbenzene hydroperoxide. However, excess dehydrogenation of ethylbenzene leads to the production of phenylacetylene (PA). Presence of phenylacetylene causes problem during extraction of styrene as phenylacetylene is very tough to separate from the styrene stream because of their analogous properties. In addition to the high costs for to removal of phenylacetylene from the styrene stream, even a small amount of PA in the ethylbenzene monomer act as a cross-linker and may halt the chain growth which is requisite for styrene formation. Accordingly, any polymerization catalysts used in the styrene production process will get poisoned and deactivated, restraining the maximum allowable limit to below 10 ppm.

Various techniques/catalyst has been known to be used to selectively remove Phenylacetylene from styrene. One such technique includes selective catalytic hydrogenation of Phenylacetylene.

Metals spanning Palladium (Pd), Platinum (Pt), Nickel (Ni), and Gold (Au) are known for their hydrogenation properties. Nickel based catalysts has been extensively investigated for alkynes hydrogenation for their ability to dissociate H2 molecules. Phenylacetylene's selective conversion to styrene have been tested on nickel silicon intermetallic catalyst. There has been increased study on Phenylacetylene conversion to styrene over an ultrathin Ni nano-sheets. From the catalysts of the prior art, it has been seen that after 4 hours-reaction time, the conversion of Phenylacetylene was 98%, while the selectivity to styrene and ethylbenzene were 89% and 11% respectively. Phosphide based Ni catalysts ($Ni_2P/Al_2O_3$) was selective to styrene approximately 88.2%, while Ni—$Al_2O_3$ merely showed 0.7% selectivity.

Dehydrogenation of phenylacetylene in general generates styrene and ethylbenzene as primary products, and cyclohexane, benzene, ethylcyclohexane, 1,3-diphenylpropane and 1,4-diphenylbutane as secondary/side compounds. As mentioned, presence of secondary/side compounds in the manufacturing of styrene considered as impurities. For obtaining usable styrene, additional time and money needs to be spent for removing these impurities from styrene which increases the cost of the end product. This additional process of removing impurities makes the process energy inefficient.

There is a need to manufacture a new catalyst for selectively manufacturing styrene from phenylacetylene with high conversion rate and high selectivity and at a low temperature.

SUMMARY OF THE INVENTION

The inventors have developed a new method of manufacturing styrene from phenylacetylene. The invention uses a new cerium-based bimetallic catalyst for selectively converting Phenylacetylene to styrene. The cerium-based catalyst is specifically cerium oxide doped with nickel and niobium oxide. The said method for manufacturing styrene involves contacting phenylacetylene with the cerium-based catalyst at a low temperature and at atmospheric pressure. The method further relates to phenylacetylene hydrogenation in a gas phase at low temperature and atmospheric pressure conditions.

According to one aspect of the invention there is provided a process of manufacturing styrene with high selectivity to styrene comprising:
  providing gaseous phenylacetylene;
  providing gaseous hydrogen;
  providing a cerium bimetallic catalyst;
  reacting the phenylacetylene with the hydrogen in the presence of the cerium bimetallic catalyst; and
  thereby obtaining an end product comprising a styrene fraction and a waste fraction.

The temperature may be maintained between 150° C. to 300° C. The temperature may preferably be maintained at about 300° C.

The selectivity to styrene may be in the range of 91% to 96%.

In a particular embodiment, reacting phenylacetylene with hydrogen may be carried out at atmospheric pressure.

The cerium bimetallic catalyst may be cerium metal doped with Nickel and Niobium. The cerium bimetallic catalyst may be any of Ni-5% NbCe and Ni-10% NbCe.

The styrene fraction may comprise 54% to 71% styrene of the end product.

The method may further comprise reducing the cerium bimetallic catalyst reacting with phenylacetylene and hydrogen.

The cerium bimetallic catalyst may be reduced at a temperature of 500° C.

The catalyst may be reduced with hydrogen at 500° C. for about 2 hours before reacting with phenylacetylene and hydrogen.

The catalyst may be stable for about 5 cycles of manufacturing styrene without losing selectivity to styrene and without reduced conversion rate.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Further features of the invention are described hereinafter by way of a non-limiting example of the invention, with reference to and as illustrated in the accompanying diagrammatic drawing. In the drawings:

FIGS. 3(a) and 3(b) shows a graph of XRD plot of calcined (a) and reduced samples (b), respectively;

DETAILED DESCRIPTION OF THE DRAWINGS

Figure 1:
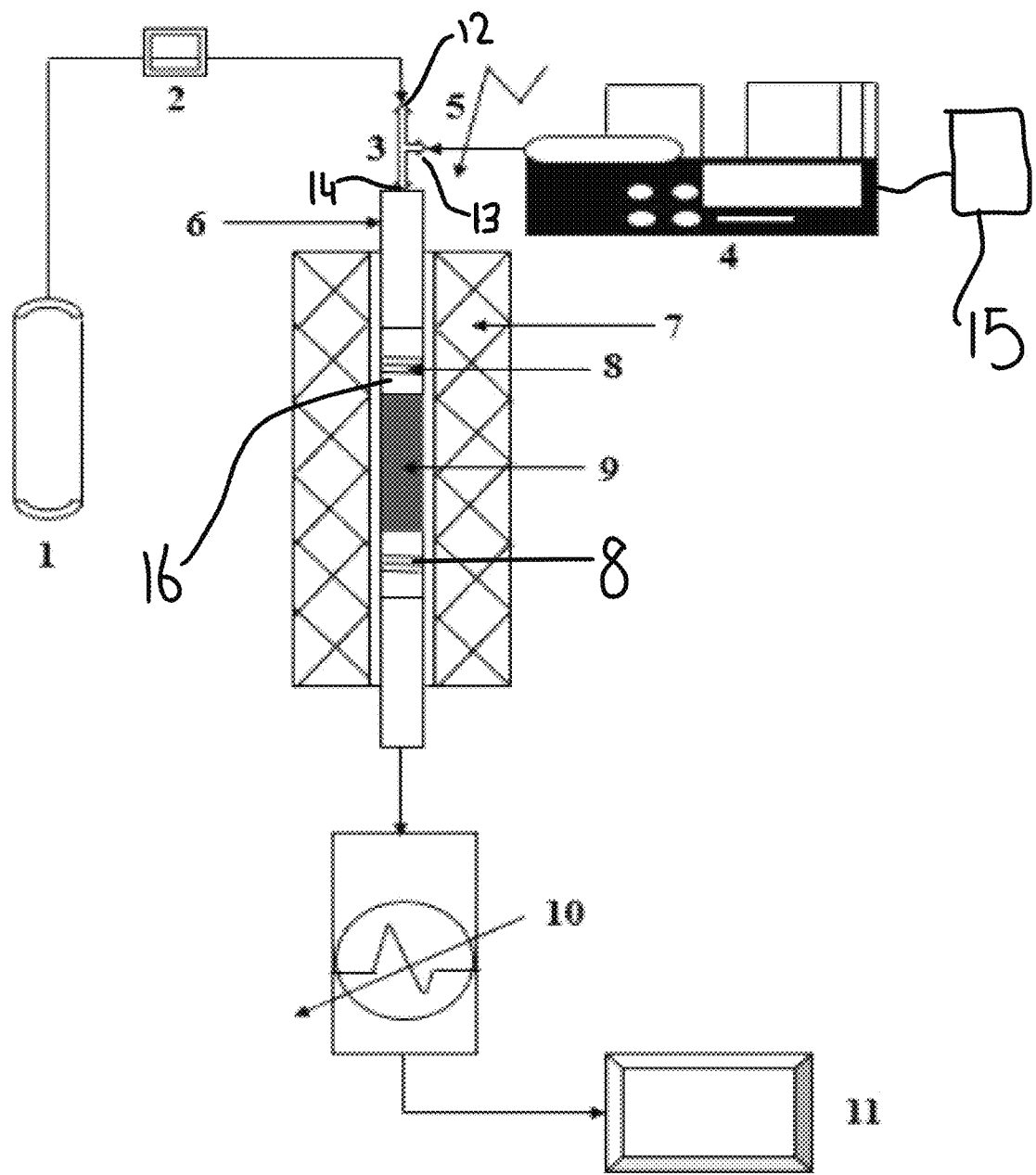
FIG. 1 shows a schematic diagram of the hydrogenation reaction system in accordance with the invention.

The invention relates to a process for selectively manufacturing styrene using a ceriumbased catalyst. The catalyst of the invention is specifically cerium based bimetallic catalyst. The cerium based bimetallic catalyst is cerium based bimetallic catalyst doped with Niobium and Nickel.

The catalyst includes cerium as the support material. Nickel and Niobium are doped onto the support material. Nickel plays an active role in the dehydrogenation reaction of phenylacetylene. Niobium promotes good interaction of Nickel onto the Cerium support. The inventors have advantageously found that doping Nickel and Niobium onto cerium provided a catalyst exhibiting a high conversion rate of phenylacetylene to styrene with a high selectivity to styrene.

The selectivity characteristics of the catalyst is based on the nature of the support. The metallic nanoparticles of Nickel and Niobium when combined with an oxide support such as cerium oxide improves the dispersion of the active phase on the support, thereby promoting thermal stability, and also disrupting the chemisorption potential. Cerium (IV) oxide ($CeO_2$) is specifically chosen as a base for its potential to switch from Ce4+ ($CeO_2$) to $Ce_{3+}$ ($Ce_2O_3$) oxidation states under reducible atmosphere. This reduction leads to the formation of a non-stoichiometric $CeO_2$-x oxides (with x values is between 0 and 0.5) via the creation of Oxygen (O) vacancies on the oxide surface. These vacant O sites are the most reactive in metallic oxides.

Effective use of $CeO_2$ as a support depends on the metal-support interaction capacity. Relative to other supports known in the prior art, $CeO_2$ shows high adhesion energy as well as inhibited sintering process during $H_2$ treatment. Strong Metal-Support Interaction (SMSI) has been explained to upshot from electronic (charge transfer between the support and metallic nanoparticles) or geometric effect (capping of the metallic nanoparticles with functional groups from the support) depending on the reduction temperature.

Niobium (Nb) based catalysts are known to be applied in catalytic operation. Analysis with density functional theory (DFT) revealed that incorporating Nb atoms on $CeO_2$ leads to the formation of a Ce—Nb bond with the electron transfer from Nb to Ce. Tetrahedral O atoms established an upturn in electronegativity and this expedites the catalytic propensity of the $NbCeO_2$.

Nickel has been identified has an active metal towards the dissociation of hydrogen. So, the dissociated hydrogen atoms on the Ni active sites will interact with the phenylacetylene to aid its hydrogenation to styrene.

Preparing a Bimetallic Catalyst—Cerium Oxide Doped with Niobium and Nickel

Prior art provides different methods of preparing a series of Ni based catalysts supported on Aluminium based support ($Al_2O_3$). This had several drawbacks. There exists high interaction between the chloride ions and the $Al_2O_3$. Also, the chloride ions were present in the catalyst even after calcination at 600° C. Equally, Ni—$Al_2O_3$ was readily susceptible to sintering and shows high pore diameter of 50 Å. The inventors have advantageously developed in accordance with the invention a method of preparing the catalyst using cerium oxide ($CeO_2$) as a support. This support is specifically chosen for its ability to withstand sintering and its relatively inert nature while manufacturing Styrene from Phenylacetylene.

Materials Used:

Cerium oxide ($CeO_2$) powder was obtained from Sigma-Aldrich, >99%) was used as the support for all the catalysts. Ammonium niobate (V) oxalate hydrate ($C_4H_4NNbO_9$, Sigma-Aldrich, >99%) provided the Niobium precursor, and nickel chloride hexahydrate ($NiCl_2 \cdot 6H_2O$) (Sigma-Aldrich>99%) serves as the Ni precursor. The liquid phenylacetylene (Sigma-Aldrich, >99%) was supplied by Sigma-Aldrich.

Process of Preparing the Catalyst:

The catalyst is prepared by incipient wetness impregnation method also called dry impregnation method or capillary impregnation. In a general incipient wetness impregnation method, the active metal precursor is dissolved in an aqueous or organic solution. The metal precursor-containing solution is added to a catalyst support containing the same pore volume as the volume of the solution that was added. Capillary action draws the solution into the pores of the support. If the metal precursor solution is added in excess of the solution of catalyst support, the metal solution transport changes from a capillary action process to a diffusion process, which is much slower. Once the catalyst support has soaked up the metal precursor from the solution, the catalyst is then dried. The calcination is an important process designed to dry off the volatile components within the solution, depositing the metal on the catalyst surface.

Using the above method of the invention, several catalysts were prepared using cerium oxide as the support material. Example of a method of preparation of the catalyst in accordance of the invention is provided below.

Example 1—Preparing 6% Ni—Ce and 5% Ni—Ce Catalyst

To prepare Ni—Ce catalysts, a known quantity of $CeO_2$ was dissolved in de-ionized $H_2O$ and the Ni precursor was added to the solution. The mixture was stirred at 70 rpm for 1 h at room temperature. Subsequently, the $H_2O$ was steadily evaporated at 60° C. The resulting solid was dried in a hot air oven for 2 hrs at 100° C. The samples: 6% Ni—Ce and 5% Ni—Ce were prepared by this process.

Example 2—Preparing Ni-5% NbCe Catalyst of the Invention

To prepare Ni-5% NbCe catalyst of the invention, 3.64 g of $CeO_2$ was used and 0.2 g of $Nb_2O_5$ was used. These ($CeO_2$ and $Nb_2O_5$) were mixed in deionized water.

Ammonium niobate (V) oxalate hydrate ($Nb_2O_5$) was used as Niobium precursor. $Nb_2O_5$ was prepared by calcining the ammonium niobate (V) oxalate at 500° C. for 1 hr.

Ni precursor was then added to the solution of $CeO_2$ and $Nb_2O_5$. The Ni concentration was fixed at 4% for the catalysts of the invention.

The solution containing $CeO_2$, $Nb_2O_5$ and $NiCl_2$ was stirred at 70 rpm for 1 hr at room temperature. The water was steadily evaporated at 60° C. and thereafter the resulting solid was dried for 2 hr at 100° C. and calcined at 550° C. for 4 hr in air with the heating ramp rate of 5° C./min. The catalyst of the invention Ni-5% NbCe was thus prepared.

Example 2—Preparing Ni-10% NbCe Catalyst

To prepare Ni-10% NbCe catalyst of the invention, 3.44 g of $CeO_2$ and 0.4 g of $Nb_2O_5$ was used. The $CeO_2$ and $Nb_2O_5$ were mixed in deionized water. Ni precursor was then added to the solution of $CeO_2$ and $Nb_2O_5$. The Ni concentration was fixed at 4% for the Nb based catalysts. The solution containing $CeO_2$, $Nb_2O_5$ and $NiCl_2$ was stirred at rpm for 1 hr at room temperature. The water was steadily evaporated at 60° C. and thereafter the resulting solid was dried for 2 hr at 100° C. and calcined at 550° C. for 4 hr in air with the heating ramp rate of 5° C./min. The catalyst of the invention: Ni-10% NbCe was prepared using this process.

For the purpose of elucidating the invention, undoped Cerium oxide was used as a control.

Catalysts Characterization

Different spectroscopic technologies were applied to examine the physico-chemical properties of the prepared catalysts. Powder X-ray diffraction (XRD) patterns were recorded to determine the lattice parameters, and crystallite size of the sample. Quantachrome Instruments (NOVAtouch NT 2LX-1, USA) performed the $N_2$ adsorption and desorption experiment to compute the Brunauer-Emmett-Teller (BET) surface areas. The Barrett-Joyner-Halenda (BJH) was used to determine the average pore size and the pore size distribution with P/Po range of the desorption branches of 0.80-0.35. The FTIR analysis was performed with Fourier Transform Infrared Spectrometer (Jasco Corporation, Japan). A multifunctional general-purpose scanning electron microscope (SEM) by (JEOL JSM. 6010 PLUS/LA) integrated with Energy Dispersive Spectroscope (EDS) was used to perform surface and elemental analysis. In order to investigate the thermal stability and the composition of the pure and prepared samples, Thermogravimetric analysis (TGA) was carried out with TGA Q50 V20.10 Build 36 analyzer. The temperature changes between 0° C. to 800° C. at a heating rate of 10° C./min under the flow of nitrogen.

To determine the exact amount of Ni on the support after calcination, inductively coupled plasma mass spectrometry (ICP-MS) techniques were employed. Specifically, approximately 100 mg of the sample (catalyst) was dissolved in a mixture of 4 ml of hydrogen peroxide and 4 ml concentrated nitric acid. The samples were left for 12 h, after which 4 ml of concentrated hydrochloric acid was added. Then, the resulting solution was heated at 85° C. for 30 min and diluted with de-ionized water prior to analysis.

In order to understand the hydrogen consumption of Ni—Ce and Ni—NbCe catalysts, temperature program reduction (H2-TPR) profiles were obtained using a Quantachrome Chem BET-TPR/temperature-programmed desorption (TPD) chemisorption instrument. Samples of 50 mg were packed in a U-shaped quartz tube reactor, between two quartz wool plugs and were degassed at 350° C. for 1 hour under N2 flow of 30 mL $min^{-1}$. After cooling to 25° C., 5% $H_2$ in $N_2$, was allowed to flow over the sample at a rate of 50 mL $min^{-1}$ while heating up to 950° C. at a rate of 10° C. $min^{-1}$. The instrument was equipped with a thermal conductivity detector for the measurement of $H_2$ uptake.

Method of Manufacturing Styrene

FIG. 1 provides a schematic diagram of a hydrogenation reaction system for preparation of styrene in accordance with the invention.

As a non-limiting example, for illustrating the catalytic process of the cerium based bimetallic catalyst and for manufacturing styrene in accordance with the invention, a hydrogenation reaction system was used. The hydrogenation reaction system utilises a gas cylinder 1 connected to a mass flow controller 2. The gas cylinder is filled with hydrogen/Helium ($H_2$/He) gas. There is present a three-way valve 3. The three-way valve is capable of receiving the $H_2$/He gas in one opening 12, phenylacetylene through a second opening 13, and the third opening 14 is connected to a quartz tube reactor 6. The three-way valve is so connected that it receives the He/He gas and Phenylacetylene from its two openings 12, 13 respectively, and the two components ($H_2$/He gas and Phenylacetylene) are released through the third opening 14 into the quartz tube reactor. There is provided a syringe pump 4 which is connected to a reservoir 15 enabled for holding phenylacetylene. The syringe pump is connected to the second opening 13 of the three-way valve 3 so as to allow flow of phenylacetylene into the three-way valve.

The phenylacetylene may be held in the reservoir in a liquid or gaseous state. If the phenylacetylene is held in a liquid state, the syringe pump is optionally connected to a heating mechanism for raising the temperature of phenylacetylene to convert it from a liquid to a gaseous state. In a preferred embodiment, the phenylacetylene is in the gaseous state. The gaseous form of phenylacetylene is provided from the reservoir to the second opening 13 of the three-way valve.

The quartz tube reactor is maintained at atmospheric pressure. The quartz tube is fitted with a heating mechanism 7 to maintain a temperature of about 150° C.-300° C. Please note that the temperature of the quartz tube may be regulated by any mechanism, apparatus or device which does not react with the components of the system i.e. is inert to the reaction components ($H_2$/He gas, Phenylacetylene, cerium bimetallic catalyst). Non limiting examples of the heating mechanism that may be used includes and is not limited to hot jacket enclosing the reactor, an electric tube furnace, by having the reaction in an enclosed heating chamber, by incorporating electric coils or a jacket within or outside the quartz tube reactor.

The quartz tube reactor is a fixed bed reactor. it is noted that the fixed bed reactor is an example of a reactor used in accordance with the invention. The hydrogenation reactor may be used with any of the known reactors in the prior art. The catalyst (cerium bimetallic catalyst) is placed within the quartz tube reactor. The catalyst is held in position within the quartz tube reactor by means of a stopping material 8. The stopping material is any material which does not react with nor absorbs or adsorbs any components of the reactants, final product and the catalyst itself. A non-limiting example of such a stopping material is quartz wool. The stopping material is held within the quartz tube reactor, such that one section of the stopping material is provided in an area within the reactor and near the first opening of the quartz tube reactor facing the three-way valve and a second section 8 of the stopping material is provided in an area within the reactor near the end opposite the end facing the three way valve. The two sections of the stopping material are so placed such that there is a central area 16 defined by the boundaries set by the stopping material at the two opposite ends of the fixed bed reactor. In a preferred embodiment, the stopping material is maintained at a thickness of 4 micrometer at both ends.

The catalyst 9 is held in the central area. The movement of the catalyst in the quartz tube reactor is limited by the stopping material. The density and the porosity of the stopping material is so maintained that it allows for the movement of the $H_2$/He and Phenylacetylene into and outside of the stopping material but does not allow for movement of the cerium bimetallic catalyst through the boundaries set by the stopping material.

The quartz tube reactor through its second opening 18 is connected to a condenser 10. This condenser is configured to lower the temperature of the gaseous products exiting the reactor and convert it from the gaseous to liquid form.

This system may be optionally connected to different measuring and characterisation systems 11 to measure different parameters such as product composition, chemical and steric characteristics of the product, conversion rate, etc. One such non-limiting example includes Gas chromatography-mass spectrometry (GC-MS).

Method of Manufacturing Styrene in Accordance with the Invention is Described Herein As starting materials, hydrogen is mixed with a carried gas Helium and placed in a $H_2$/He cylinder. In the reservoir, phenylacetylene is stored.

Phenylacetylene is readily available in a liquid form. For making styrene in a fixed bed reactor of FIG. 1 in accordance with the invention the phenylacetylene is preferably provided in a gaseous state. If the phenylacetylene is provided in a liquid form, it may be converted into its gaseous form by heating the liquid phenylacetylene above its boiling temperature. The boiling point of phenylacetylene is 144° C. By maintaining the temperature of the phenylacetylene above its boiling temperature, a continuous stream of gaseous phenylacetylene may be obtained.

Depending on the nature of the reservoir, the phenylacetylene may be maintained in a liquid or a gaseous state. The example of the hydrogenation reaction system of FIG. 1 requires phenylacetylene in a gaseous state. It is therefore imperative that when phenylacetylene enters the second opening 13 of the three-way valve, it is in a gaseous state.

If the reservoir maintains the phenylacetylene in a gaseous state, no further mechanisms is involved for conversion of the state of the phenylacetylene. If the reservoir maintains the phenylacetylene in a liquid state, a mechanism to heat the phenylacetylene is provided before the phenylacetylene enters the three-way valve, such that the phenylacetylene is in a gaseous state while entering the valve.

Phenylacetylene may be heated and converted into a gaseous state in the reservoir or within a tube which carries the phenylacetylene from the reservoir to the second opening 13. Such heating may be brought about by a heating jacket, electric coils, heating chamber, etc. The temperature of the tube is maintained such that the internal temperature of the tube is maintained to be above the boiling temperature of the phenylacetylene i.e. at 144° C.

In accordance with the invention, in preparation of the quartz tube reactor, about 0.8 g of the catalyst was packed between the two quartz wool plugs (stopping material). The quartz tube reactor is heated by a temperature controlled electric furnace. The catalysts were reduced in-situ at 500° C. for 2 hours in a stream of 5% $H_2$ balanced in He, after which the reactor was cooled to the desired reaction temperature. In a preferred embodiment, the desired reaction temperature for conversion of phenylacetylene to styrene is 150° C.-300° C.

In another embodiment, styrene is manufactured using liquid phenylacetylene. Liquid The liquid phenylacetylene is maintained in the reservoir. liquid phenylacetylene was pumped into the reactor using a computerized syringe pump. When the liquid phenylacetylene was pumped through the reservoir through the tube, the liquid phenylacetylene was heated above its boiling point so as to convert the phenylacetylene into gaseous state. In a preferred embodiment, evaporation of the liquid phenylacetylene was achieved with a digital temperature-controlled heating tape operated at 250° C.

The flow rate of the gaseous phenylacetylene was maintained at 30 μL/min.

The 3-way valve receives gaseous phenylacetylene and the carrier gas $H_2$/He. The gaseous phenylacetylene and carrier gas is collectively termed as the reactant stream. Within the 3-way valve, the reactant stream before entering the quartz tube reactor consists of gaseous phenylacetylene and carrier gas $H_2$/He. The flow of the reactant stream is maintained at 50 mL/min of 5% $H_2$ balanced in He (3752.25 mL g-1 h-1).

Inside the quartz tube reactor, the temperature is maintained from about 150° C.-300° C. and the pressure is maintained at atmospheric pressure.

In the presence of the cerium bimetallic catalyst, at 150° C.-300° C. and at atmospheric pressure, the gaseous phenylacetylene reacts with Hydrogen to selectively form styrene.

As the product (styrene) is a gaseous form, there is provided a condenser connected to the quartz tube reactor after the opening 18 to collect the exhaust gas. The exhaust gas comprises of the end product (styrene) and a waste fraction. The waste fraction may comprise of non-reacted phenylacetylene, hydrogen gas, etc. as non-limiting examples. The condenser is maintained at a temperature lower than the quartz tube reactor, so as to condense the hot gas exiting the reactor. In accordance with the invention, it was surprisingly found that the liquid obtained after condensation was composed substantively of styrene.

The following equation was used to calculate the efficiency of phenylacetylene (PA) conversion and Styrene (ST) and Ethylbenzene (ET) selectivity $$PA \text{ conversion}(\%) = \frac{[PA]_{in} - [PA]_{out}}{[PA]_{in}} \quad (1)$$

$$ST \text{ selectivity}(\%) = \frac{[ST]_{in}}{[PA]_{in} - [PA]_{out}} \quad (2)$$

$$EB \text{ selectivity}(\%) = \frac{[EB]_{in}}{[PA]_{in} - [PA]_{out}} \quad (3)$$

Figure 2:
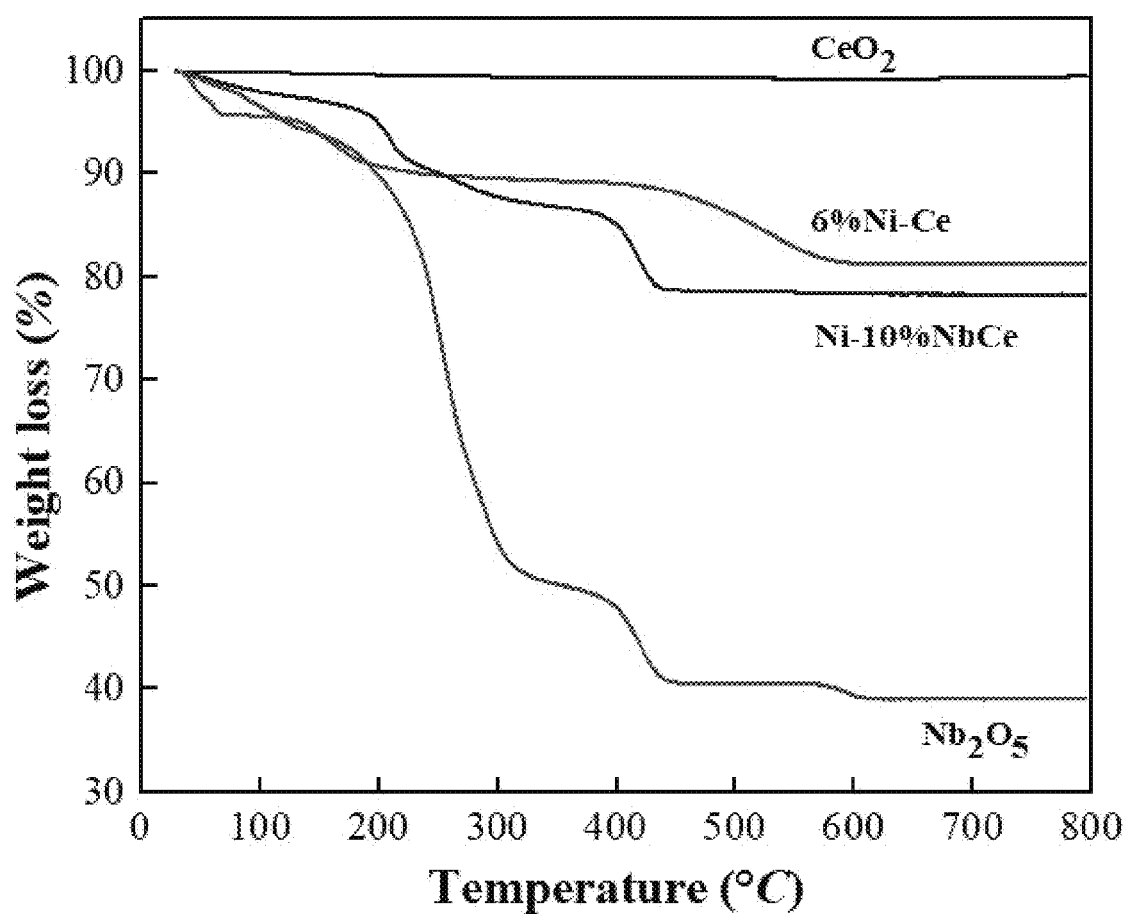
FIG. 2 shows a graph of TGA result of the calcined catalysts in accordance with the invention.

TG analysis was used to investigate the decomposition temperature of the prepared samples of the catalyst. It is seen that metallic precursor might contain different anions whose presence may inhibit catalyst performance. FIG. 2 discusses the thermal gravimetric (TG) analysis of calcined catalysts. More specifically, FIG. 2 shows the thermogravimetric analysis (TGA) result of different catalysts of prior art ($CeO_2$, 6% NiCe, $Nb_2O_5$) and the cerium bimetallic catalyst of the invention in the range of 25° C. to 800° C. It is seen that $CeO_2$ shows high purity and exhibits negligible weight lost due to the intrinsic high thermal stability. This is suggestive that $CeO_2$ crystallinity is present after the calcination. $Nb_2O_5$ shows a significant weight loss with a residual weight of about 35%. This indicates that only pure $Nb_2O_5$ is present after the calcination. The decomposition step between 25° C. and 320° C. is ascribed to the loss of crystalline and physically absorbed $H_2O$ molecules. The weight loss observed between 320° C. and 600° C. is the loss of the carbon content present in the $Nb_2O_5$ precursor. Depositing metallic Ni on the $CeO_2$ necessitates the abstraction of the chloride anions (Cl−) from the prepared samples. Usually, Cl− is released in the form of $Cl_2$ or HCl and the Ni metal is oxidized to NiO.

Only the prepared samples with the highest loading of Ni and Nb were analyzed for TGA. The weight loss observed for the 6% Ni—Ce and Ni-10% NbCe observed below 280° C. is the surface and water of crystallization. Weight loss above this region is the decomposition of the CI ions that leads to the transformation of $NiCl_2$ to NiO.

FIG. 3. discusses the results of X-ray diffraction analysis pattern for pure $CeO_2$, $Nb_2O_5$ and the Ni and Nb doped cerium oxide catalysts of the invention. The evolution of the metal species was examined for the calcined and reduced samples. The intense peaks observed for both the calcined and the reduced Ni—$CeO_2$ are 28.6°, 33.1°, 47.5°, 56.3°, 59.1°, 69.4°, 76.7° and 79.1° which are attributed to (111), (200), (220), (311), (222), (400), (331), and (420) crystal planes, respectively, of the typical face-centered cubic $CeO_2$ (JCPDS card No. 34-0394). The NiO peak is the (PDF #44-1159) while the Ni peak is (PDF #04-0850). The sharpness of the peak is indicative that the NiO and Ni exists in the crystalline phase. The peaks of the Nb atoms are absent in all the prepared samples, possibly due to the high dispersion on $CeO_2$. This suggests that the inclusion of the Nb atoms do not distort the crystallinity of $CeO_2$. As previously provided, X-ray diffraction (XRD) peak of Nb is only observable on $CeO_2$ at 50 wt % loading of Nb. The lattice parameters were computed from the XRD peaks in order to investigate the doping effect. The inter-planar spacing was evaluated with the Bragg's law; Equation 4, and the lattice parameter was calculated with Equation 5. The crystallite sizes of the samples was calculated with the Scherrer's equation (Equation 6) by applying the full width at half maximum (FWHM).

$$d = \frac{n\lambda}{2\sin\theta} \quad (4)$$

d is the inter-planar spacing, λ is the wavelength, a is the lattice parameter and h,k,l are the miller indices, β is the full width at half maximum, k is the Scherrer constant, D is the crystallite size and θ is the Bragg or diffraction angle. The equations were applied to the peak highest intensity; $CeO_2$ (111) plane. The crystallite size and the lattice constants for the samples are depicted in Table 1.

TABLE 1

Crystallite size and the lattice constant of the prepared catalysts

| Sample | Lattice constant (Å) | Crystallite size (nm) |
| --- | --- | --- |
| $CeO_2$ | 5.4085 | 35.37 |
| 6% Ni—Ce | 5.4119 | 40.36 |
| 5% Ni—Ce | 5.4106 | 35.91 |
| Ni—5% NbCe | 5.4062 | 34.84 |
| Ni—10% NbCe | 5.4066 | 35.13 |

The calculated lattice parameter of $CeO_2$ is 5.4085 Å which is in reasonable agreement with the value of 5.41 Å for $CeO_2$. Introducing Ni and Nb into $CeO_2$ presents contrasting but interesting scenario. The inventors have surprisingly found that the lattice parameter of $CeO_2$ was found to expand correspondingly with the loading of Ni. This is ascribed to the replacement of $Ce^{4+}$ (1.01 Å) ions with the $Ni^{2+}$ (0.72 Å) ions, and the simultaneous creation of oxygen vacancies, so as to attain electrical neutrality, this promotes the reduction of $Ce^{4+}$ to $Ce^{3+}$. Doping of Nb atoms to Ni—Ce brought about a contraction in the lattice parameter. In view of the lower value of Nb ionic radius to Ni (0.64 Å vs 0.72 Å), the possible reason for this trend could arise from the competition between Nb and Ni atoms on the $CeO_2$ surface. This leads to the saturation of the $Ce^{4+}$ sites and inhibits interstitial sites. Ultimately, the crystal lattice undergoes strain, which leads to a lattice distortion in order to relieve the strain, and subsequently, contraction in the lattice parameter. The crystallite size of all the prepared samples shows only slight variation among themselves, with only the sample with 6% Ni as exemption. The 6% Ni—Ce has the highest crystal size of 40.36 Å while Ni-5% NbCe possesses the lowest size, in agreement with the expansion and contraction of the lattice parameter observed for the Ni and Nb catalysts, respectively. We note here that the correlation in the crystallite size removes the possibility of crystal growth with the incorporation of Ni and Nb into $CeO_2$, except for the 6% Ni—Ce catalysts.

Figure 4:
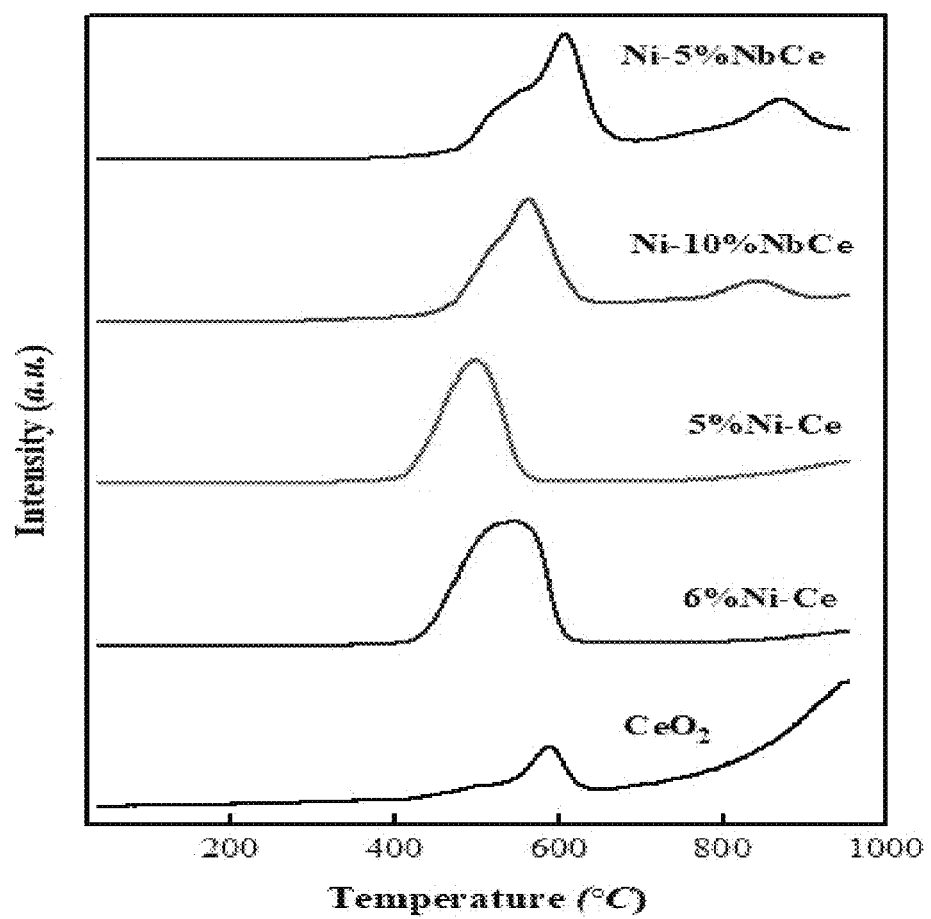
FIG. 4 shows a graph of TPR profiles of the prepared catalyst samples.

FIG. 4 discusses results of temperature programmed reduction of catalyst samples. As shown in FIG. 4, the $H_2$-Temperature-programmed reduction (TPR) profiles of the prepared samples are examined up to 950° C. Reduction of pure $CeO_2$ shows a peak signal around 580° C. which typifies the reduction of surface oxygen. The peak observed at higher temperature starting from around 810° C. is ascribed to the reduction peak of bulk cerium oxide. Usually, the reduction of NiO to Ni occurs around 390° C.-750° C. The intensity of the interaction between the active phase and the support is contingent upon the temperature where the consumption of hydrogen is observed. $H_2$ consumption at rather too low temperature connotes a poorly bonded active metal to the support while reduction at higher temperature confirms a strong metal support interaction. As observed, all the prepared catalysts exhibit reasonable consumption of hydrogen, confirming the reduction of NiO to Ni. Reduction of NiO to Ni starts at lower temperature (about 10° C.) for the 5% Ni—Ce than the 6% Ni—Ce, owing to the small difference in the particle size of both samples as conformed via the XRD. This is corroborated by the broader peak observed with the catalyst with higher Ni loading. It is seen from the prior art Singha et al. that the $H_2$-TPR of 5% Ni—Ce, 5% Ni—$CeO_2$ prepared by impregnation and coprecipitation method, induced higher temperature of reduction of NiO to Ni, in contrast to the co-precipitated catalyst. The reduction peak of the impregnation approach shows a broader and low intensity peak. This was ascribed to the unrestrained deposition of Ni particle on $CeO_2$ which ensued into different particles sized Ni that got reduced at expansive temperature range. Likewise, agglomeration was found to prevent the exposure of Ni particles during the TPR analysis. Although, 5% Ni—Ce is reduced at lower temperature, the peak shows both a lower intensity and broadness compared to the 6% Ni—Ce counterpart. Thus, the lower temperature observed is pegged only to the incident of lower loading of Ni and the slight difference in crystallite size.

The reduction peak of $Nb_2O_5$ for $H_2$-TPR presents contrasting values, depending on commercial source of the niobium precursor and if the $Nb_2O_5$ is used in pure form or as a support. From the prior art, in some cases, a reduction peak of superficial species of niobium is seen at 477° C. while in other cases no reduction was observed even at 500° C. This discrepancy was explained with the difference in the origin of the precursor. Unsupported and calcined $Nb_2O_5$ showed no reduction peak at 600° C., but a reduction peak was found around 897° C. Doping $Nb_2O_5$ with other materials affords the reduction peak to be observed at lower temperature. Platinum supported $Nb_2O_5$ shows the reduction of $Nb_2O_5$ at around 400° C. Accordingly, a variant is observed between the Ni—Ce and the Ni—NbCe catalysts reduction profiles.

Inclusion of the Nb atoms promotes good interaction of Ni with the $CeO_2$ support. It is observed that while the reduction of NiCe catalysts begins at 400° C. and extends to about 600° C., the reduction of Nb catalysts occurs at 450° C. and prolongs to about 700° C. This occurrence presents a dual possibility of either the reduction at high temperature is contingent upon the interaction between Ni and $Nb_2O_5$ or is due to the interaction with the $CeO_2$ support. Ni is reported to offer good interaction with $Nb_2O_5$ when exposed to H2 atmosphere. Reduction was found to occur only on the Ni2+ ions that bonds weakly to a sub-layer $Ni^{2+}$ ions strongly attached to the $Nb_2O_5$ support, which could render the catalyst passive due to lower reduction. The reduction of the weakly adsorbed or surface Ni ions on $Nb_2O_5$ occurs between 300° C.-350° C. It could be inferred from the temperature at which the reduction peak is observed that both the surface and strongly bond Ni ions were exposed to $H_2$. Interestingly, the reduction of Ce from +4 to +3 oxidation states usually initiated around 800° C., was found only on the Nb doped catalysts, confirming the bulk reduction of $CeO_2$. It is seen that incorporating Nb atoms into $CeO_2$ could confer a switch from $Ce^{4+}$ to $Ce^{3+}$ due to the transfer of electrons from the 4d states of Nb to the 4f states of $CeO_2$. Also, reduction at higher temperature for the Nb catalysts suggests the presence of large proportion of Ni—Ce—O solid solution and an oxygen vacancies, indicating, that nickel species are highly dispersed in the $CeO_2$ framework. Thus, the SMSI observed on Nb doped catalysts might be from the electronic effect and geometric effect.

TABLE 2 displays the amount of H2 consumed by different catalysts.

| Catalyst sample | Hydrogen consumed (μmol/g) |
| --- | --- |
| 5% Ni—Ce | 8050.91 |
| 6% Ni—Ce | 9906.02 |
| Ni—5% NbCe | 5129.53 |
| Ni—10% NbCe | 5912.42 |

Table 2 indicates that the hydrogen consumption increases proportionally with the Ni content in the sample. The catalyst with the highest Ni content shows a consumption of 9906.02 μmol/g while the samples with the lowest Ni content reveals lesser consumption. The temperature at which $H_2$ consumption occurs give the clue that the reduction is both for NiO and $CeO_2$ surface oxygen. Analysis of the Nb catalysts reveals another possibility. The Ni content in these samples was maintained at 4%, however, the $H_2$ consumption increases with the Nb content. This is indicative that in addition to NiO, surface oxygen of both $CeO_2$ and $Nb_2O_5$ might have been reduced in the process.

TABLE 3

BET and Ni content of the prepared samples

| Catalysts | BET (m2/g) | Theoretical value (Ni content) | ICP-MS (Ni content) |
| --- | --- | --- | --- |
| $CeO_2$ | 50.4 | — | — |
| $Nb_2O_5$ | 38.6 | — | — |
| 6% Ni—Ce | 32.8 | 6 | 5.8 |
| 5% Ni—Ce | 42.3 | 5 | 4.9 |
| Ni—10% NbCe | 45 | 4 | 4.0 |
| Ni—5NbCe | 48.5 | 4 | 3.9 |

Table 3 indicates the textural properties of the prepared catalysts and their Ni contents determined by inductively coupled plasma mass spectrometry (ICP-MS). The Ni content measured experimentally agrees with the theoretical values and deviations are within ±0.2. The Brunauer-Emmett-Teller (BET) surface area of all the samples reveals that doping $CeO_2$ with Ni and/or Nb alters their properties. Doping of $CeO_2$ with Ni initiates reduction in the surface area and with further loading, continuous decrease is observed. This might be due to the decrease in the amount of $CeO_2$ content in the sample and the blocking of the pores of $CeO_2$ by the Ni particles.

Figure 5:
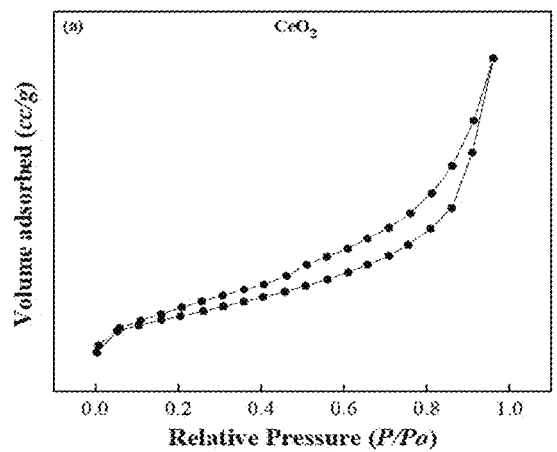
FIGS. 5(a) to 5(f) show graphs of N2 adsorption-desorption isotherms of the prepared catalyst samples.
Figure 5:
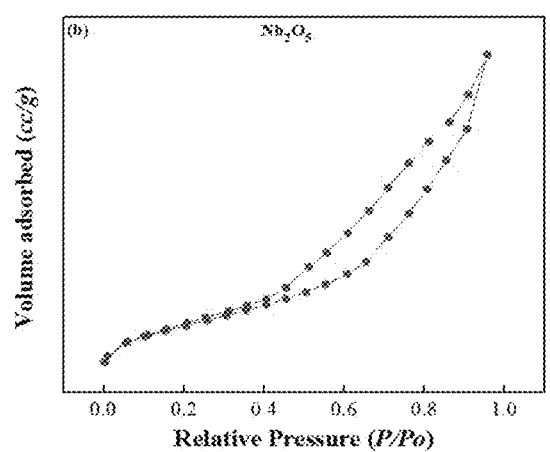
Figure 5:
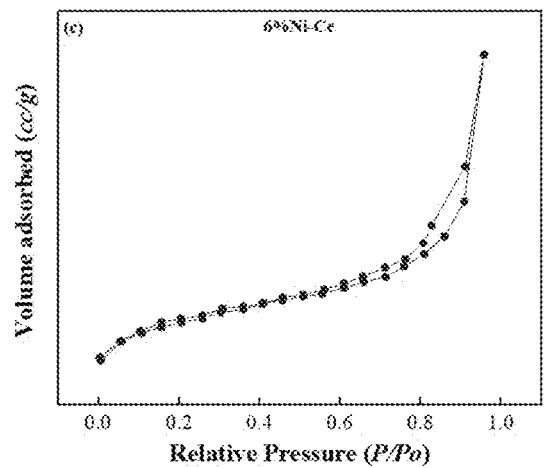
Figure 5:
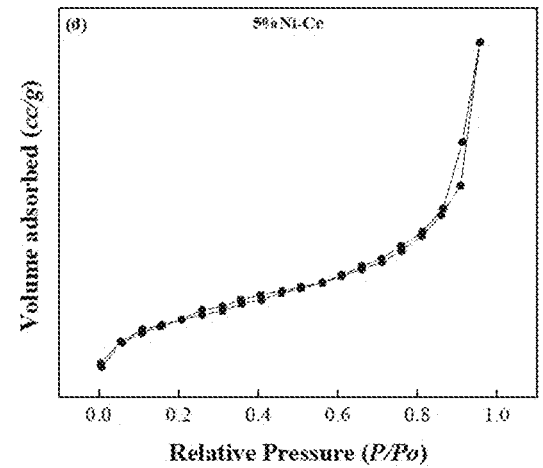
Figure 5:
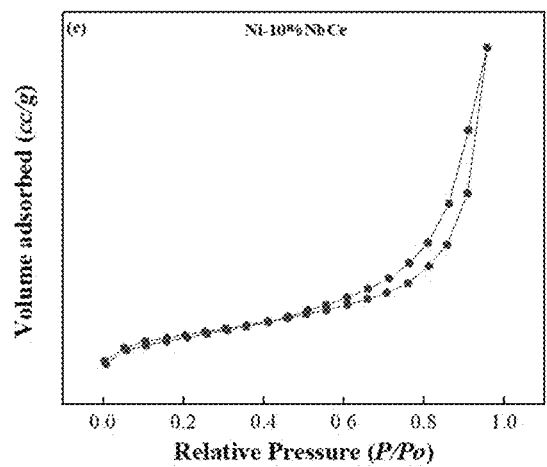
Figure 5:
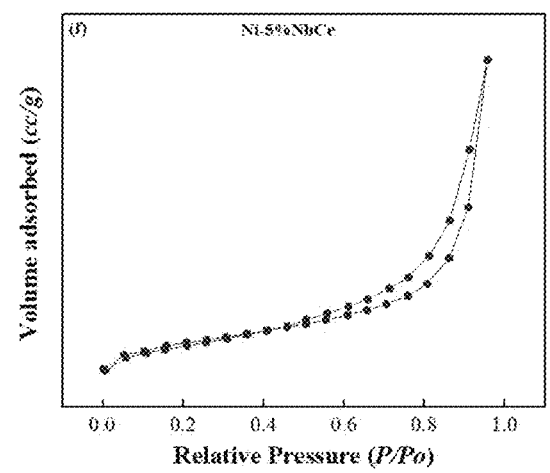

FIG. 5 is the N2 adsorption-desorption measurement of the prepared catalyst materials. All the samples exhibit type IV isotherm ascribed to the capillary condensation in mesopores. Hysteresis loop of type $H_3$ is found for both pure $CeO_2$ and $Nb_2O_5$ samples. This confirms that the sample contains mesopores with silt-like shapes. Introducing Ni and Nb into $CeO_2$ lattice changes the hysteresis loop from $H_3$ to $H_1$. Mono-molecular layer adsorption is promoted on the Ni—NbCe samples (Ni-5% NbCe, Ni-10% NbCe) owing to the steady rise in their isotherm in contrast to the sharp increase in the Ni—Ce catalysts. However, all doped samples reveal multi-molecular layer adsorption upon the saturation of the mono layer.

Figure 6:
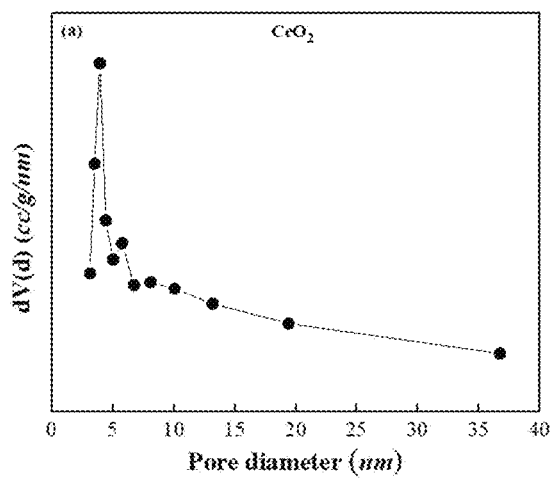
FIGS. 6(a) to 6(f) show graphs of pore size distribution of the prepared catalyst samples.
Figure 6:
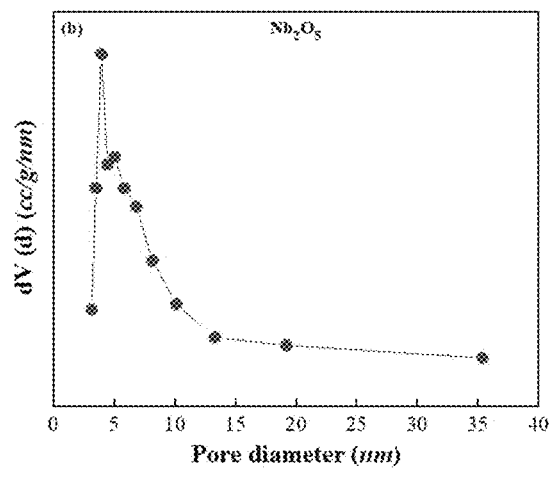
Figure 6:
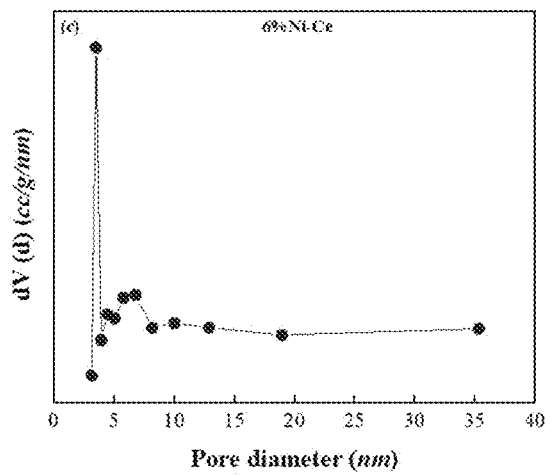
Figure 6:
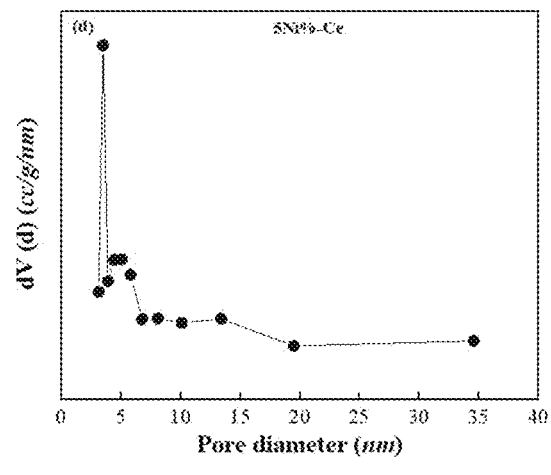
Figure 6:
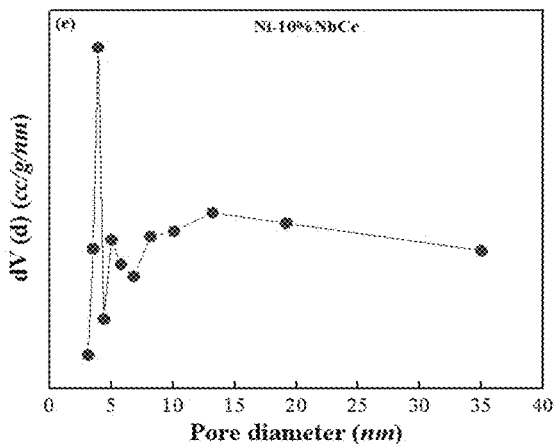
Figure 6:
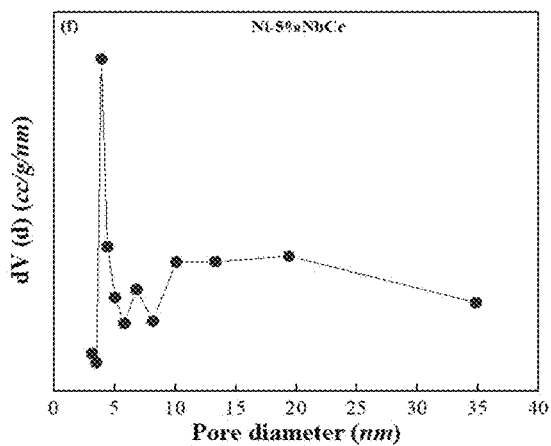

Investigation of the corresponding pore size distribution of all the formulated samples was evaluated with the BJH method, and the result are shown in FIG. 6. The particle sizes dominate within 3-10 nm range, indicating that the samples mainly contains of mesopores with a few micropores and macropores.

Figure 7:
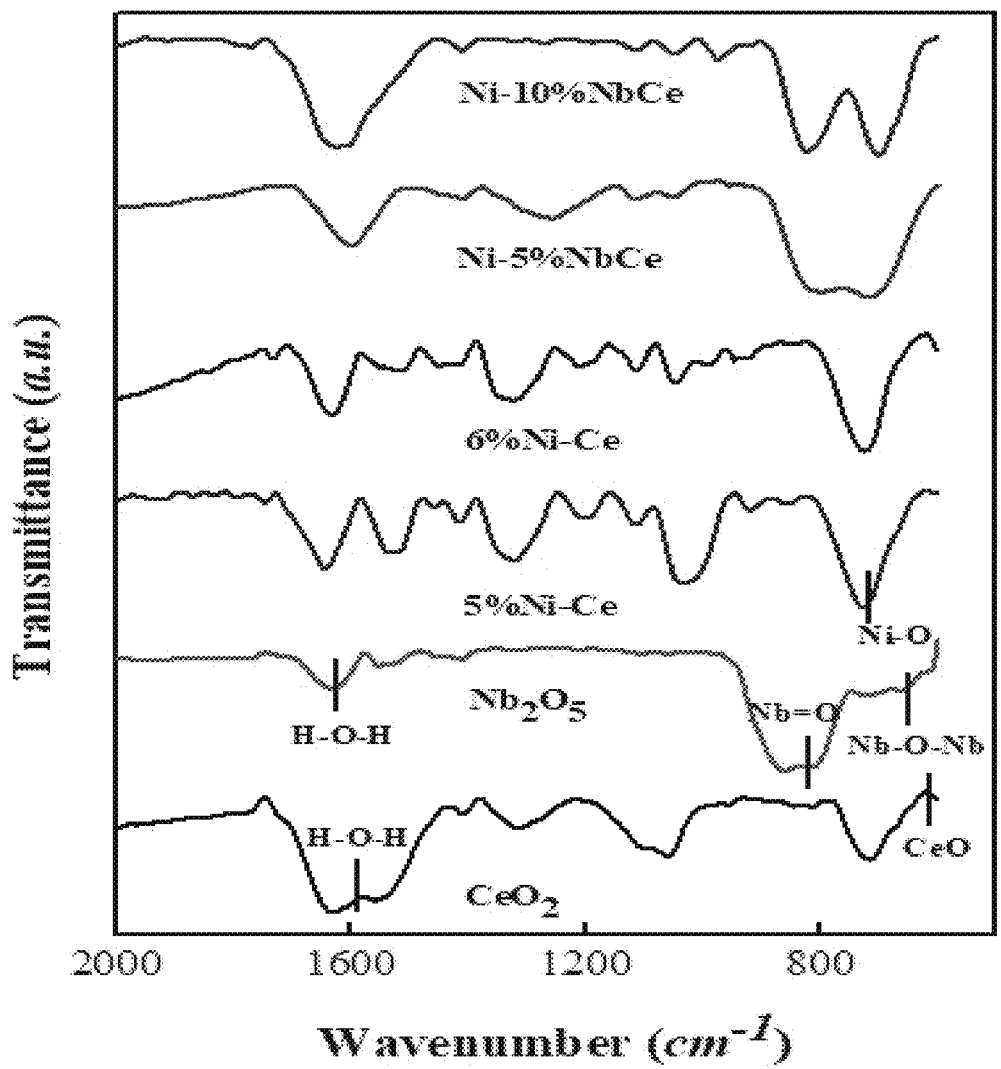
FIG. 7 shows a graph of FTIR spectra of the control and prepared catalyst samples.

FIG. 7 discusses the Fourier Transform Infrared Spectroscopy (FTIR) analysis of the prepared catalyst samples. To ratify the functionalization of the $CeO_2$ nanoparticles with nickel and niobium, the FTIR spectra of the pure and doped samples were recorded in the range 400-4000 cm-1 wavenumber. The important peaks pertinent to metal-oxygen bonds usually observed around 2000-400 cm-1 wavenumber are shown in FIG. 7. The spectrum of $CeO_2$ is representative of a typical $CeO_2$ pattern.

The H—O—H peak around 1624 $cm^{-1}$ is the interlayer stretching and bending vibration of molecular water. The peak at about 500 $cm^{-1}$ is the Ce—O stretching vibrations. The crystallinity nature of $Nb_2O_5$ is confirmed from the spectrum due to the peaks observed. In the range of 800-950 cm$^{-1}$ the vibrational stretching of Nb=O surface species is observed which is related to the highly distorted octahedral NbO$_6$ structures. The metal-oxygen-metal bond of niobium species that extends between 600-700 cm-1 is assigned to the Nb—O—Nb bridges from the slightly distorted octahedral NbO$_6$ that is connected with the sharing corners. To integrate the possibility of the formation of nickel nanoparticles on CeO$_2$, generally, the bands of NiO occurs below 800 cm$^{-1}$ due to inter-atomic vibrations. The peak observed at 610 cm$^{-1}$ is allotted to the Ni—O stretching band of the NiO nanoparticles. It is noted that this band overlaps the CeO$_2$ spectrum around this region, however, the intensity of the peak after incorporating the Ni species becomes prominent, confirming the formation of NiO nanoparticles. Addition of Nb species impact the spectra differently. The broad peak that extends in the region of 850-500 cm$^{-1}$ is found to encompass the Ce—O, Nb—O—Nb and NiO peaks earlier identified, this suggests the formation of bimetallic Ni—NbCe nanoparticles.

FIG. 8a-8f discusses the scanning electron microscope (SEM) results of the prepared catalyst samples. The scanning electron microscopy was used to determine the morphology of the samples.

Figure 8:
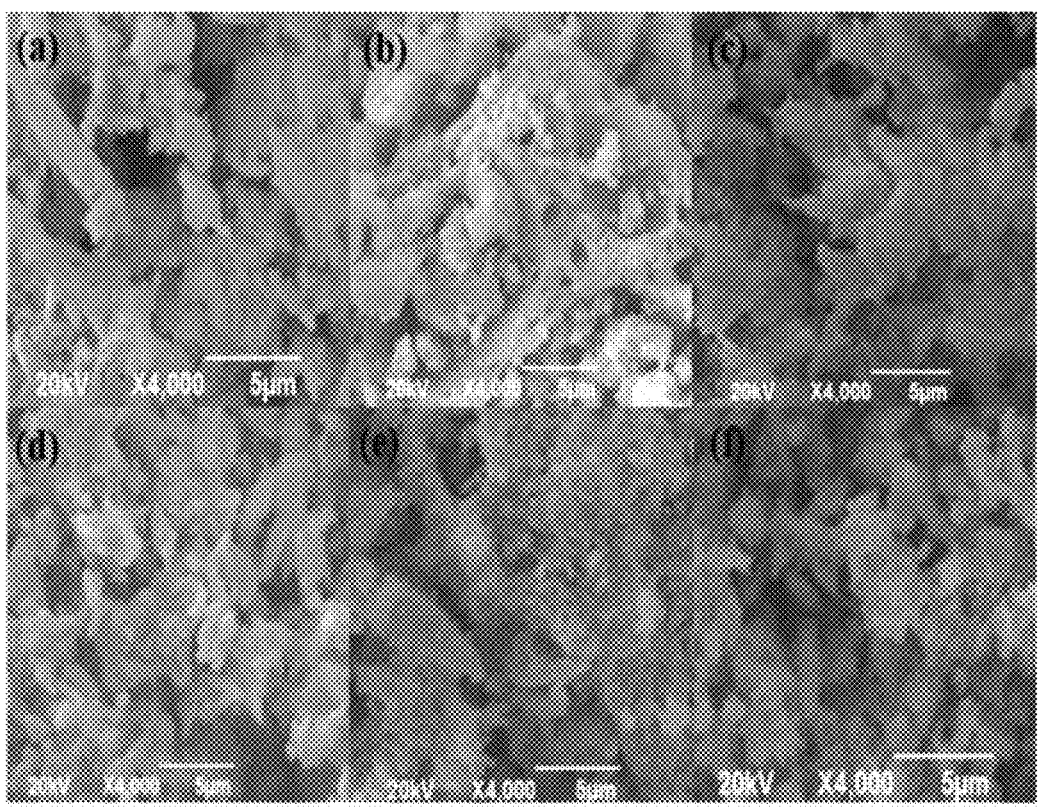
FIGS. 8(a) to 8(f) show SEM image of; $CeO_2$ 8(a); $Nb_2O_5$ 8(b); 6% Ni—Ce 8(c); 5% Ni—Ce 8(d); Ni-10% NbCe 8(e); and Ni-5% NbCe 8(f)

FIG. 8a is the stand-alone CeO$_2$ where the image reveals that homogeneity exists at the sample surface, eliminating the possibility of the varying particle size distribution. The spherical shape nanoparticles are absent on the surface of the CeO$_2$. It is seen in the prior art that a non-homogenous irregularly shaped CeO$_2$ nanoparticles could be directed to give spherically shaped nanoparticles by using the calcination temperature 600° C. By employing co-precipitation method, it is observed that the spherically shaped CeO$_2$ nanoparticles predominates on the surface of the calcined samples as against the prepared samples. Preparation of CeO$_2$ samples via hydrothermal method was found to give irregularly shaped particles and the instances of spherical nanoparticles were only seen after the addition of ethylenediamene which served as the capping agent. However, the variance of this result with the CeO$_2$ SEM image might have ensued because of the different preparation technique employed.

FIG. 8b is the image of Nb$_2$O$_5$. The surface contains pores/voids which are available for interaction with other adsorbed molecules.

The 6% Ni—Ce catalyst in FIG. 8c exhibits a fine smooth structure with some clusters identified on the surface. This particle aggregation might be responsible for the higher crystallite size obtained from the XRD analysis. This phenomenon becomes less conspicuous when the Ni content is decrease in the 5% Ni—Ce sample, FIG. 8d. The Nb doped samples in FIG. 8e and FIG. 8f show the fine and homogenous structures devoid of agglomeration.

Figure 9:
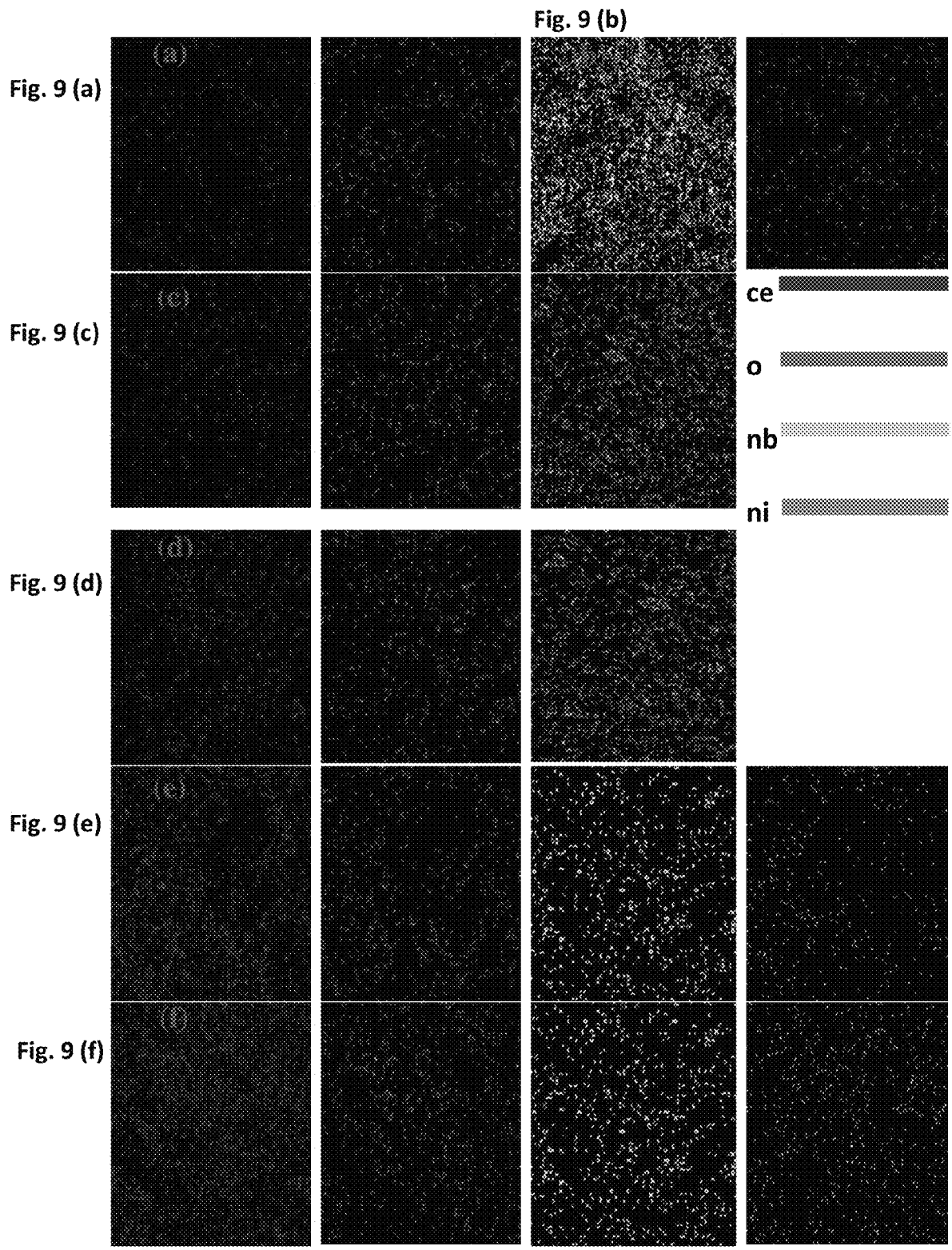
FIGS. 9(a) to 9(f) show EDS mapping of, $CeO_2$ 9(a); $Nb_2O_5$ 9(b); 6% Ni—Ce 9(c); 5% Ni—Ce 9(d); Ni-10% NbCe 9(e); and Ni-5% NbCe 9(f)

The Energy-dispersive X-ray spectroscopy (EDS) mapping of all the samples are shown in FIGS. 9a-9f. FIG. 9a provides EDS mapping of CeO$_2$; FIG. 9b provides EDS mapping of Nb$_2$O$_5$; FIG. 9c provides EDS mapping of 6% Ni—Ce; FIG. 9d provides EDS mapping of 5% Ni—Ce; FIG. 9e provides EDS mapping of Ni-10% NbCe and FIG. 9f provides EDS mapping of Ni-5% NbCe. The samples show a uniform distribution of the component elements. In particular, the homogenous distribution of the CeO$_2$ species will afford the close interaction of the Ni and Nb particles and creates a conducive environmental suitable for catalytic performance. In all the areas on the maps, no sample shows any dot intensity, suggesting that the EDS analysis could not identify the aggregated spots observed on the SEM image of the 6% Ni—Ce catalyst.

Figure 10:
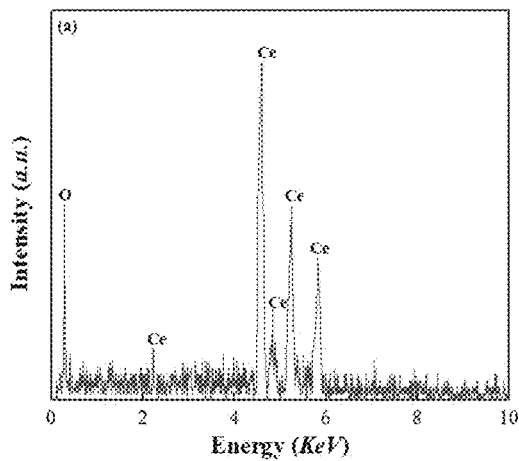
FIGS. 10(a) to 10(f) show graphs of EDS profile of the prepared catalyst samples.
Figure 10:
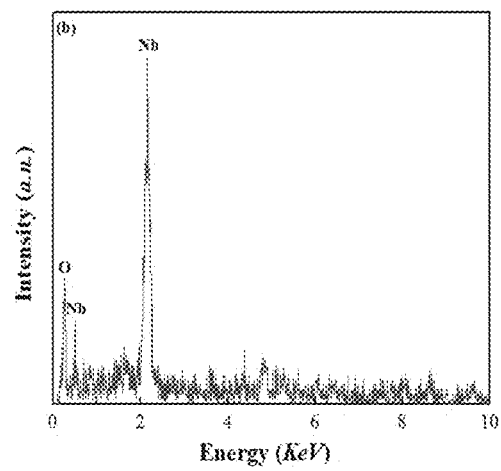
Figure 10:
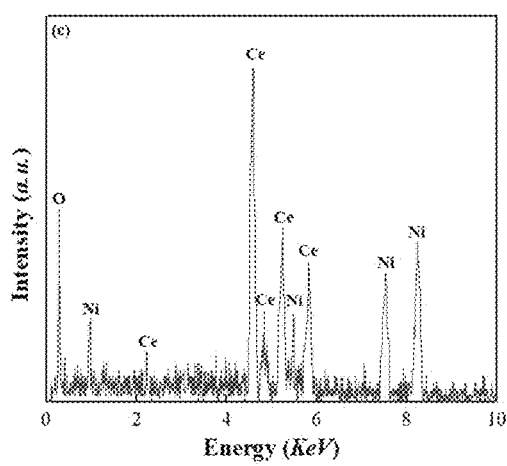
Figure 10:
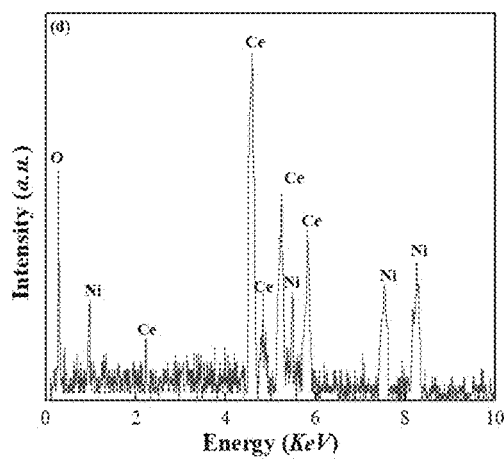
Figure 10:
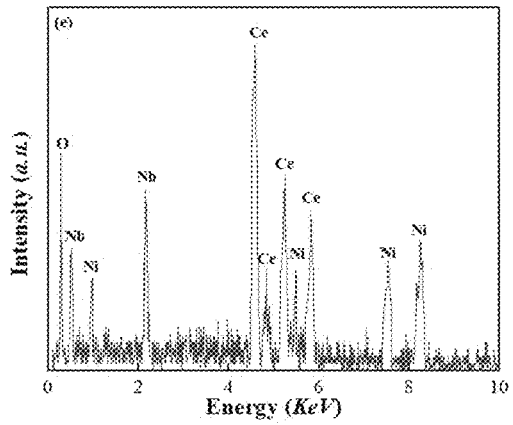
Figure 10:
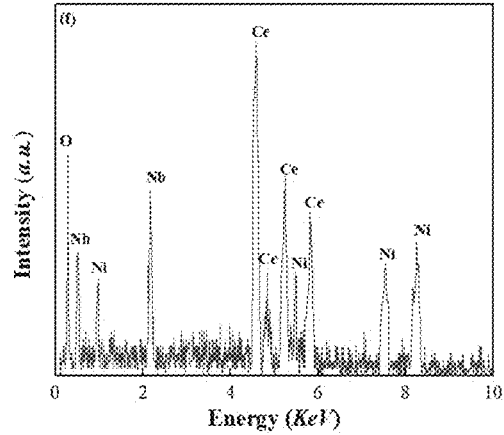

The EDS profile depicted in FIG. 10 is the point analysis of the prepared samples. It is confirmed that the Ni and Nb atoms observed on the samples are found at their characteristic energy values, indicating that they are successfully doped on the CeO$_2$. The peak intensity observed for all the samples commensurate quantitatively according to their metal contents in all the samples.

Figure 11:
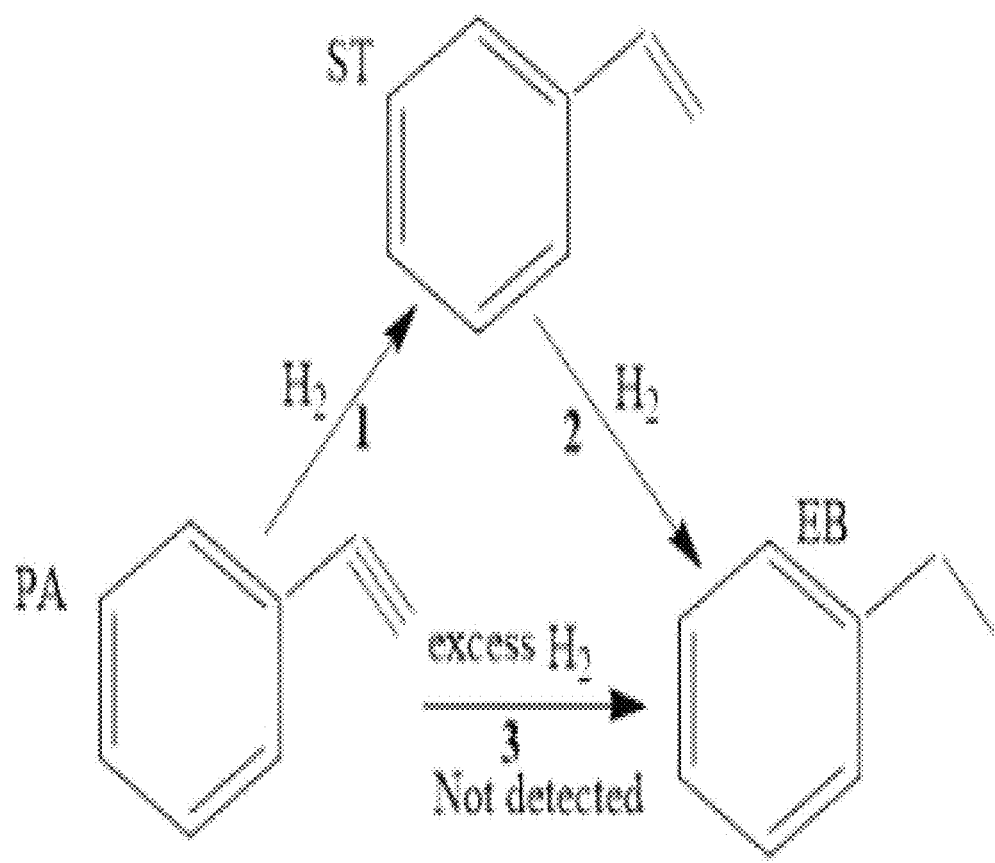
FIG. 11 shows schematic representation of phenylacetylene hydrogenation routes.

FIG. 11. discusses different routes for hydrogenation reaction of phenylacetylene. Selective hydrogenation of phenylacetylene can yield different reaction products. Styrene and Ethylbenzene are the main products obtained on hydrogenation of phenylacetylene. Other products obtained by the hydrogenation process include cyclohexane, benzene, ethylcyclohexane, 1,3-diphenylpropane and 1,4-diphenylbutane. As depicted in FIG. 11, there are two potential routes for the hydrogenation reaction. In the first route (1) Phenylacetylene is converted to Styrene and eventually Styrene gets converted to Ethylbenzene. The reaction is spontaneous in that, the flow of hydrogen can either direct the products to styrene and then to ethylbenzene (1-2-3), or the reactions goes directly to the undesired product, ethylbenzene (1-3). An ideal catalyst for the reaction is expected to direct the pathway to 1-2 and inhibits both 2-3 and 1-3 pathways.

Styrene is a valuable semi-product with a high industrial importance. Ethylbenzene is a poisonous byproduct of the reaction, Presence of ethylbenzene will contaminate the phenylacetylene as well as halt the overall reaction. Any good hydrogenation catalysts should enhance the selectivity to Styrene and inhibits/reduce the formation of ethylbenzene.

In reference to FIG. 11, in the second route (2), phenylacetylene is over hydrogenated to form Ethylbenzene without any yield of Styrene.

In accordance with the invention and to elucidate the catalytic performance of the prepared Ni and Nb doped CeO$_2$ catalysts, hydrogenation reaction was carried out in the range of from about 150° C.-300° C. and at 1 atmospheric pressure. Analysis of the products after the hydrogenation process reveals that Styrene and Ethylbenzene are the main products obtained on hydrogenation of Phenylacetylene. Other products were not detected by the GC-MS and the possible formation of oligomers is ruled out. Oligomers tends to bind to the surface of the catalysts and initiate loss of active site, leading to decrease in Phenylacetylene conversion. It was seen that there was no loss of activity of cerium bimetallic catalyst over 5 cycles. Therefore, it can be concluded based on this and GC-MS analysis that there were no oligomers formed.

Calculation of Efficiency of Conversion and Selectivity

The conversion of phenylacetylene to styrene and selectivity of phenylacetylene (PA) to styrene (ST) and Ethylbenzene (ET) were calculated with using equations 1-3 provided below.

$$PA\ \text{conversion}(\%) = \frac{[PA]_{in} - [PA]_{out}}{[PA]_{in}} \quad (1)$$

$$ST\ \text{selectivity}(\%) = \frac{[ST]_{in}}{[PA]_{in} - [PA]_{out}} \quad (2)$$

$$EB \text{ selectivity}(\%) = \frac{[EB]_{in}}{[PA]_{in} - [PA]_{out}} \quad (3)$$

Figure 12:
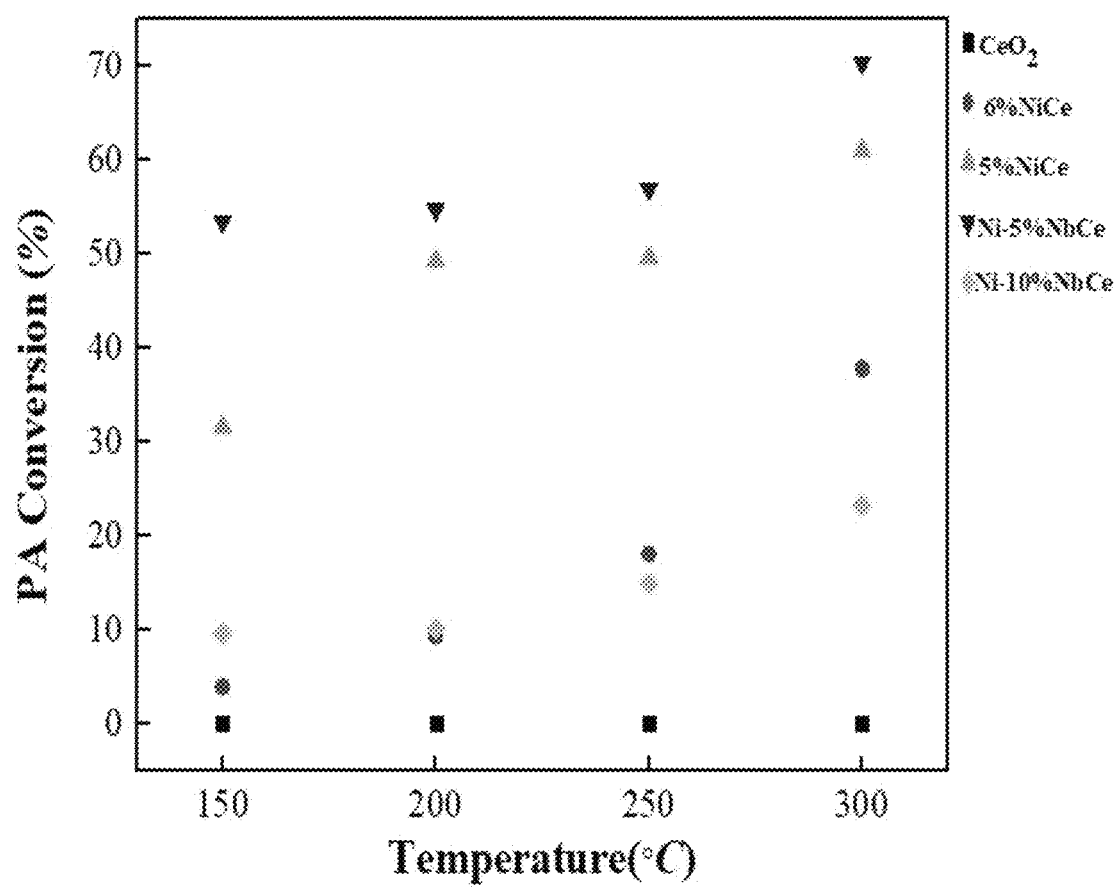
FIG. 12 shoes a graph of conversion of phenylacetylene over the prepared catalysts samples.

FIG. 12 shows the conversion rate of Phenylacetylene using the cerium bimetallic catalyst (Ni-5% NbCe, Ni-10% NbCe) in comparison with $CeO_2$, 6% NiCe, 5% NiCe.

It is observed that the conversion of Phenylacetylene to styrene increases with a rise in temperature using all catalyst. This increase in conversion rate is postulated to be due to the reaction equilibria dependency on temperature. Thus, the instance of activity loss due to oligomer formation is eliminated. The 6% Ni—Ce catalyst shows 4% conversion at 150° C. and increased to 38% at 300° C., while the counterpart, 5% Ni—Ce reveals a conversion of 32% and 62% at 150° C. and 300° C., respectively.

It is known that Ni doped $CeO_2$ catalysts undergoes deactivation primarily because of the aggregation of active metal phase and carbon deposition occurring at higher temperature. However, operating at low reaction temperature would eliminate the instances of carbon deposition. Thus, the decline in the conversion at higher metal content could be ascribed to the blocking of pore, and metal aggregation on the surface which leads to decrease in the surface area. This is corroborated with the result of BET analysis. Further, Nickel (Ni) contents between 1.83-3.61 wt % performed optimally, while increasing the Ni amount to between 5.28-14.5 wt % negatively impacted the activity of the catalysts for $CO_2$ reforming to $CH_4$. Ni content of 5.0 w % was found to efficiently hydrogenate carbon oxides. The beneficial effect at lower Ni loading can be attributed to the creation of more active sites and the ease of activation of the triple bond of the Phenylacetylene.

It is known that that Pt—Ni nanoframe (NF)@$CeO_2$ was effective in PA hydrogenation. Although, a high conversion of PA was achieved but the selectivity to Styrene was maximum only at 56.8%. The high conversion of Pt+ and Ni species realized was ascribed to the $CeO_2$ shell which was found to offer strong interfacial transfer of charge with the Pt—Ni nanoframe. This signifies that $CeO_2$ support would have influence the high activity.

The inventors have advantageously developed the catalyst by incorporating Niobium into the Ni—$CeO_2$ matrix. The concentration of Nickel was maintained at about 1.5% to 4.5% for these catalysts. The concentration of Ni was preferably maintained at 4%. Any disparity observed during conversion of phenylacetylene to styrene is not solely ascribed to the effect of Ni, rather, the synergistic effects of both the Ni and Nb atoms.

The active metals Niobium and Nickel have high affinity for $H_2$ dissociation. The Ni active sites on the cerium oxide catalyst serves as $H_2$ dissociation centres that creates activated Hydrogen surface species. The activated Hydrogen species undergoes the spill over mechanism to the surrounding Niobium active sites and binds weakly to these sites. Thus, both the Nickel and Niobium sites are now available for the hydrogenation of Phenylacetylene.

The conversion on Ni-5% NbCe at 150° C. is 54% and increased to 71% at 300° C. This superior performance to the Ni—NbCe catalysts might be due to the higher interaction with the $CeO_2$ support shown during the Temperature programmed reduction (TPR) experiment and the unique electronic properties of the Niobium atoms. The observed reduction peak of bulk $CeO_2$ creates oxygen vacancies and increases the concentration of Ce3+ ions. Hence, promoting the activity of the cerium bimetallic catalyst.

The conversion value presented here after Niobium atoms were added might appear to be at variance with usual trend of declined in alkynes conversion during hydrogenation after diluting the active metals with the less active counterparts. This is because each catalyst system has a unique behaviour contingent on their electronic tendencies.

It is seen from FIG. 12 that operating at 10% Nb content negatively impacts the activity or the conversion rate. This may be due to the over saturation of the $CeO_2$ surface with Nb atoms. It is seen that the hydrogenation reactions catalyzed by metallic catalysts are fixated on their ability to dissociate $H_2$ molecules and their capacity to add active hydrogen atoms to the adsorbed reactants. The $H_2$ dissociation tendency of Ni atoms might have become minimal after increasing loading to 10% which limited the conversion of phenylacetylene.

Figure 13:
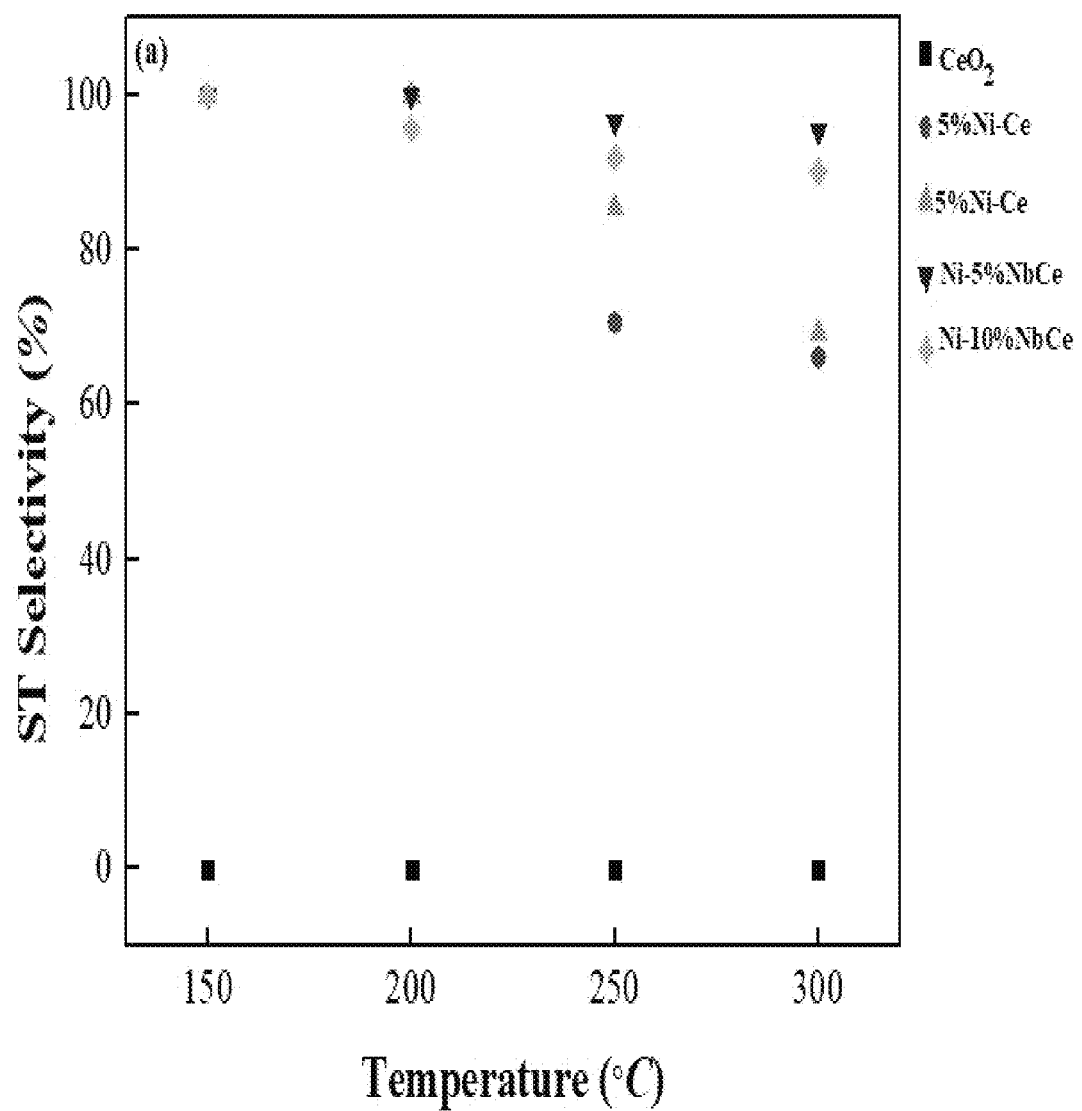
FIG. 13a shows a graph of the selectivity to styrene using different catalyst as a function of temperature.
FIG. 13b shows a graph of the selectivity to ethylbenzene using different catalyst as a function of temperature.
Figure 13:
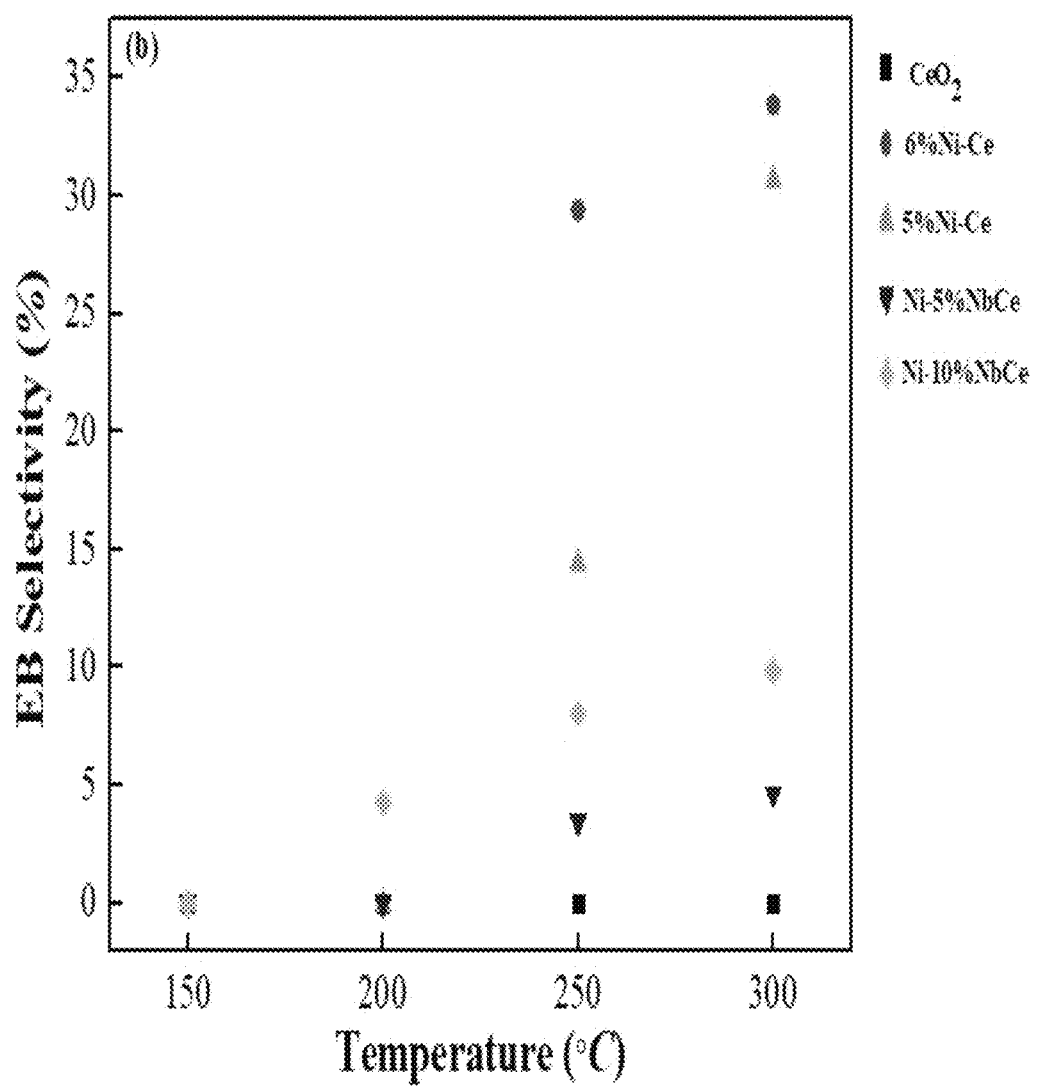

FIG. 13a shows a graph of selective conversion to styrene as a function of the temperature. For comparison purpose, different catalyst were selected including the cerium bimetallic catalyst. The catalyst used included $CeO_2$, 6% Ni—Ce, 5% Ni—Ce, Ni-5% NbCe and Ni-10% NbCe.

All the catalysts show reasonable selectivity to Styrene. At a temperature of 150° C.-200° C., the selectivity was 100% for the catalysts except for $CeO_2$. It is observed that the selectivity is reduced as the temperature of the system is increased. Contrary to general norm, it is found that the selectivity to styrene is maintained 96% and 91% even at 300° C. for the catalysts Ni-5% NbCe and Ni-10% NbCe catalysts, respectively. On the other hand, 6% Ni—Ce and 5% Ni—Ce catalysts, the selectivity to styrene reduced to 66% and 70%, respectively.

The enhanced selectivity of the cerium bimetallic catalyst confirms that the alkenes double bond reduction on Nb atoms is inhibited. Thus, any styrene formed is prevented from further interacting with the Ni—NbCe surface, while easily undergoing desorption. Accordingly, the styrene formed using the cerium bimetallic catalyst is prevented from being converted to ethylbenzene. This selectivity to styrene may be attributed to the electronic effect of charge transfer from the Nb ions to the $CeO_2$. The Nb atoms minimize the Ni—Ni ensemble effect that might otherwise lead to excessive hydrogenation. Furthermore, expending Density-functional theory (DFT) studies, the presence of Nb on amino complexes reveal that hydrogenation of phenylacetylene to Styrene is inhibited with the energy barrier of (113.1 kJ/mol) while the conversion of Styrene to Ethylbenzene suffers a higher energy barrier (132.7 kJ/mol). The hydrogenation of Phenylacetylene was exergonic than Styrene and Styrene hydrogenation was the rate determining step. This confirms that the hydrogenation to Ethylbenzene demands higher energy on Nb based catalysts. As the higher energy requirement is not provided by the catalyst of the invention, further hydrogenation of styrene is inhibited.

Similarly, FIG. 13b shows a graph of selective conversion of styrene to ethylbenzene as a function of the temperature. For comparison purpose, different catalyst were selected including the cerium bimetallic catalyst. The catalyst used included $CeO_2$, 6% Ni—Ce, 5% Ni—Ce, Ni-5% NbCe, and Ni-10% NbCe.

All the catalysts show no selectivity to Ethylbenzene when the temperature is 150° C. However, as the temperature rises, it is observed that the selectivity to ethylbenzene increases in some catalyst. It is seen that Ceria oxide shows no selectivity to ethylbenzene at temperature ranges 150° C. to 300° C. Contrary to general norm, it is seen that the selectivity to ethylbenzene is as low as 0 to about 5% for the catalyst Ni-5% NbCe, and 0 to about 10% for the catalyst Ni-10% NbCe. Accordingly, it is seen that high selectivity of the catalysts Ni-5% NbCe and Ni-10% NbCe is maintained even at high temperatures.

Table 4 compares the results obtained from the hydrogenation of phenylacetylene over different catalysts configuration. Phenylacetylene (PA) hydrogenation is mostly studied in the liquid phase where the PA-$H_2$-catalysts are in the liquid-gas-solid phases, respectively. For the catalyst of prior art, when liquid phenylacetylene is used directly into the reactor system, the liquid Phenylacetylene is dissolved in a suitable solvent such as dichloromethane. Gaseous $H_2$ is introduced into the reaction system at a high pressure to enhance its solubility in the liquid phase. The high pressure is essential as this increases the collision frequency between the catalyst surface and the $H_2$ molecule. This eventually increases the hydrogenation rate.

TABLE 4

Phenylacetylene hydrogenation reported at optimum conditions over different catalysts

| Catalysts | Conversion (%)/ TOF ($S^{-1}$) of Phenlacetylene | % Selectivity to Styrene | Temperature (° C.)/$H_2$ Pressure (MPa) | Phase of reaction |
|---|---|---|---|---|
| 5% Nb—NiCeO$_2$ | 71 | 96 | 300/0.1 | Gas |
| Ni/ND_300 | 60 | 80 | 300/0.1 | Gas |
| Fe@C | 99 | 86 | 300/0.1 | Gas |
| Pt—Ni—Ag$_{4.9}$ | 100 | 86.5 | room temperature/0.1 | Liq. |
| NF@CeO$_2$ | | | | |
| Pd$_1$Au$_{11}$NR CeO$_2$ | 99.3 | 96.8 | 90/1 | Liq. |
| Ni$_2$P/Al$_2$O$_3$ | 100 | 88.2 | 100/0.3 | Liq. |
| 250-NiSi$_x$ | 0.017 | 89.0 | 50/0.41 | Liq. |
| Pd/α Al$_2$O$_3$ | ca. 96 | ca. 70 | 50/0.1 | Liq. |
| Pt/oCNTs | 99 | 88 | 40-70/0.6 | Liq. |
| Ni:Pd 30:70 | 0.99 | 97.3 | 50/0.1 | Liq. |
| Pd/TiO$_2$ | 100 | 90 | 30/0.5 | Liq. |

As observed in Table 4, the high $H_2$ pressure in the liquid phase reaction promotes the Phenylacetylene conversion, expectedly above the conversion obtained using the catalyst of the invention. However, it is seen that the cerium bimetallic catalyst has high selectivity to styrene as compared with the different catalysts.

The catalytic potential of the prepared catalysts was subjected to kinetics analysis. The results obtained provided the quantitative insight into understanding the catalyst's ability to selectively hydrogenate Phenylacetylene to Styrene. The values of the reaction rate and the rate constant obtained at the highest temperature of the reaction, 300° C. are shown in Table 5. The Ni-10% NbCe catalyst gives the highest reaction rate of 8.896E-06 mol·s$^{-1}$·g$^{-1}_{cat}$ which is about 4 times higher than the counterpart at the higher Niobium loading, confirming that Phenylacetylene was maximally consumed at lower Niobium loading. Similarly, 5% loading of Ni on CeO$_2$ gives the reaction rate of 7.715E-10 mol·s$^{-1}$·g$^{-1}_{cat}$ which is 1.62 times the value obtained for 6% Ni—Ce catalyst. The SMSI of the Nb doped catalysts, and the improved electron transfer facilitates the higher phenylacetylene conversion observed and the Ni doped CeO$_2$ catalyst owes their high conversion to the ability of nickel to activate hydrogen on the catalyst surface. Exceeding optimum loading of these metals on the catalysts limits both their activity capacity.

TABLE 5

Rate of reaction and rate constant for stand-alone cerium (IV) oxide and the supported catalysts in phenylacetylene hydrogenation at 300° C.

| Catalysts | Reaction rate (mol · s$^{-1}$ · g$^{-1}_{cat}$) | Rate constant, k (L · s$^{-1}$ · g$^{-1}_{cat}$) |
|---|---|---|
| CeO$_2$ | 0 | 0 |
| 6% Ni—Ce | 4.781E-06 | 8.441E-07 |
| 5% Ni—Ce | 7.715E-06 | 2.173E-06 |
| Ni—5% NbCe | 8.896E-06 | 3.294E-06 |
| Ni—10% NbCe | 2.945E-06 | 4.217E-07 |

Figure 14:
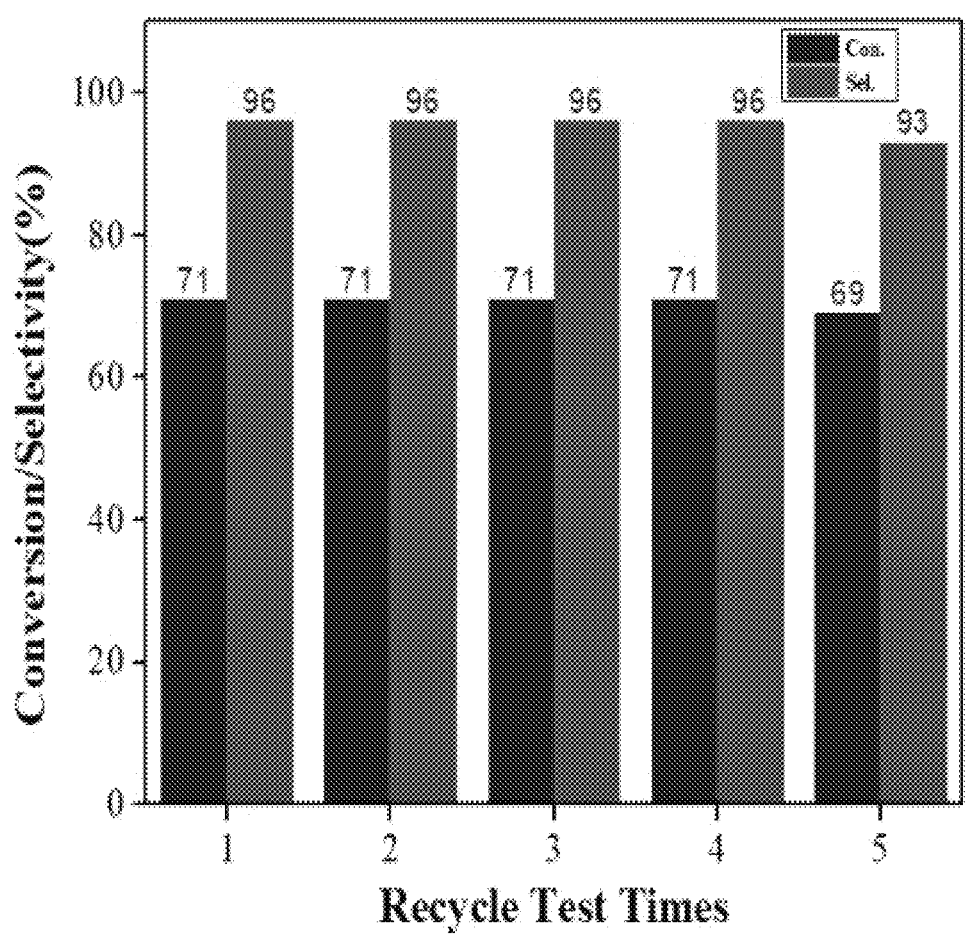
FIG. 14 shoes the conversion and selectivity vs recycling times over Ni-5% NbCe under reaction conditions: Phenylacetylene flowrate: 30 μl/min, temperature 300° C., H2 pressure 1 ATM (0.1 MPa).

The reusability of the optimum catalyst, Ni-5% NbCe was determined by recycling for five times under the same operating conditions. The conversion of phenylacetylene and selectivity toward styrene (for reaction conducted at a temperature of 300° C.; $H_2$ pressure: 0.1 MPa) over Ni-5% NbCe catalyst are shown in FIG. 14. The Phenylacetylene conversion rate and Styrene selectivity only reduced by 2%. Also, after 5 cycles of the reaction, a slight decrease in Styrene selectivity was found. The styrene selectivity decreased from 96% in the first cycle to 93% on the fifth cycle. This indicates that the catalyst exhibit stability and reusability.

It will be understood that the above embodiment descriptions are given by way of example only and that various modifications may be made by those skilled in the art. Although various embodiments have been described above with a certain degree of particularity, or with reference to one or more individual embodiments, those skilled in the art could make numerous alterations to the disclosed embodiments without departing from the scope of this invention. It is to be understood that any feature described in relation to one example may be used alone, or in combination with other features described, and may also be used in combination with any features of any other of the examples, or any combination of any other examples.

What is claimed is:

1. A process of manufacturing styrene with high selectivity to styrene comprising:
   providing gaseous phenylacetylene;
   providing gaseous hydrogen;
   providing a cerium bimetallic catalyst comprising cerium metal doped with Nickel and Niobium;
   reacting the phenylacetylene with the hydrogen in the presence of the cerium bimetallic catalyst; and
   thereby obtaining an end product comprising a styrene fraction and a waste fraction.

2. A method of claim 1, wherein a temperature is maintained between 150° C. to 300° C.

3. A method of claim 1, wherein a temperature is maintained at about 300° C.

4. A method of claim 1, wherein the selectivity to styrene is in the range of 91% to 96%.

5. A method of claim 4, wherein cerium bimetallic catalyst is any of Ni-5% NbCe and Ni-10% NbCe.

6. A method of claim 1, wherein reacting phenylacetylene with hydrogen is carried out at atmospheric pressure.

7. A method of claim 1, wherein styrene fraction comprises 54% to 71% styrene of the end product.

8. A method claim 1, further comprises reducing the cerium bimetallic catalyst before reacting with phenylacetylene and hydrogen.

9. A method of claim 1, wherein the cerium bimetallic catalyst was reduced at a temperature of 500° C.

10. A process of claim 1, wherein the catalyst is reduced with hydrogen at 500° C. for about 2 hours before reacting with phenylacetylene and hydrogen.

11. A process of claim 1, wherein the catalyst is stable for about 5 cycles of manufacturing styrene without losing selectivity to styrene and without reduced conversion rate.

* * * * *